US010601971B2

(12) United States Patent
Hatch et al.

(10) Patent No.: US 10,601,971 B2
(45) Date of Patent: Mar. 24, 2020

(54) PORTABLE ELECTRONIC DEVICE HOLDER WITH ASSISTANCE REQUEST BUTTON AND METHOD POWERING PORTABLE ELECTRONIC DEVICE

(71) Applicant: Hatchmed Corporation, Seattle, WA (US)

(72) Inventors: Brian Hatch, Seattle, WA (US); Kyrylo Keydanskyy, Seattle, WA (US)

(73) Assignee: HATCHMED CORPORATION, Seattle, WA (US)

( * ) Notice: Subject to any disclaimer, the term of this patent is extended or adjusted under 35 U.S.C. 154(b) by 126 days.

(21) Appl. No.: 16/035,283

(22) Filed: Jul. 13, 2018

(65) Prior Publication Data
US 2019/0104213 A1    Apr. 4, 2019

Related U.S. Application Data

(60) Provisional application No. 62/567,670, filed on Oct. 3, 2017.

(51) Int. Cl.
*H01R 13/46* (2006.01)
*H01R 13/62* (2006.01)
(Continued)

(52) U.S. Cl.
CPC ............. *H04M 1/04* (2013.01); *A61B 5/7445* (2013.01); *G06F 1/1632* (2013.01);
(Continued)

(58) Field of Classification Search
CPC ... H04M 1/04; H04M 1/72541; A61B 5/7445; A61B 5/74; G06F 1/1632; G06F 1/1633;
(Continued)

(56) References Cited

U.S. PATENT DOCUMENTS 3,316,044 A   4/1967 Carbary et al.
3,942,751 A   3/1976 Fay
(Continued)

FOREIGN PATENT DOCUMENTS

CN   201479176   5/2010
CN   202949471   5/2013
(Continued)

OTHER PUBLICATIONS

"Camera SnakeClamp," Snake Clamp, Retrieved from Internet: <URL:https://web.archive.org/web/20121220014228/https://snakeclamp.com/Category/camera-snakeclamp-withflexible-gooseneck-arm#.WeENSuT2Z9A>, Dec. 12, 2012, 3 pages.
"Quality Gaming and Multimedia Accessories", CTA®, [online] ctadigital.com, Retrieved from the Internet: <URL:http://web.archive,org/web/20160424204832/http://www.ctadigital.com:80/,, Apr. 24, 2016, 5 pages.
"RAM® Torque ¾™—1' Diameter Handlebar/Rail are with 1", Ball Medium Arm and X-Grip® Mounts, rammount.com, [online] RAM® Mounts, rammount.com, Retrieved from the Internet: <URL:https://web.archive.org/web/20160616011725/http:www.rammount.com/part RAM-B-408-75-1-UN7U>, Jun. 6, 2016, 3 pages.
(Continued)

Primary Examiner — Angel R Estrada
(74) Attorney, Agent, or Firm — Kilpatrick Townsend & Stockton LLP

(57) ABSTRACT

A portable electronic device (PED) holder assembly and related methods. A PED holder assembly includes a PED holder assembly to which a PED is detachably attachable, an output connector adapted for connection to an input port of a PED held by the PED holder assembly, an assistance request button attached to the PED holder assembly, a connection cable assembly operatively connected to the output connector and the assistance request button, and a bed-side connector assembly adapted to be connected to a bed-side end of a multifunctional assistance request cable. The bed-side connector assembly is operatively connected to the output connector, via the connection cable assembly, to transmit power received from the multifunctional assistance request cable to the PED. The bed-side connector is operatively connected to the assistance request button to transmit an assistance request signal generated via a pressing of the assistance request button through the multifunctional assistance request cable.

20 Claims, 16 Drawing Sheets

(51) Int. Cl.
   *H04M 1/04* (2006.01)
   *A61B 5/00* (2006.01)
   *G08B 25/01* (2006.01)
   *G06F 1/16* (2006.01)
   *G08B 25/08* (2006.01)
   *A61G 7/05* (2006.01)
   *H04M 1/725* (2006.01)

(52) U.S. Cl.
   CPC ............ *G08B 25/016* (2013.01); *G08B 25/08* (2013.01); *A61G 7/0524* (2016.11); *A61G 2203/20* (2013.01); *H01R 13/6205* (2013.01); *H01R 2201/12* (2013.01); *H04M 1/72541* (2013.01)

(58) Field of Classification Search
   CPC .... G08B 25/016; G08B 25/08; A61G 7/0524; A61G 2203/20; H01R 13/6205; H01R 2201/12; H01R 13/46; H02G 3/08; H02G 3/081
   USPC ... 174/59, 480, 482, 500, 501, 503, 50, 520, 174/58, 61; 220/3.2, 3.3, 4.01; 248/906, 248/200; 5/503.1, 658
   See application file for complete search history.

(56) References Cited

U.S. PATENT DOCUMENTS

| | | | |
|---|---|---|---|
| 4,680,790 | A | 7/1987 | Cover et al. |
| 5,273,354 | A | 12/1993 | Herrmann et al. |
| 5,701,991 | A | 12/1997 | Helmetsie |
| 5,802,636 | A | 9/1998 | Corbin et al. |
| 5,867,821 | A | 2/1999 | Ballantyne et al. |
| 6,206,464 | B1 | 3/2001 | Santa Rosa et al. |
| 6,339,410 | B1 | 1/2002 | Milner et al. |
| 6,407,335 | B1 * | 6/2002 | Franklin-Lees ..... A61M 5/1413 174/50 |
| 6,486,792 | B1 | 11/2002 | Moster et al. |
| 6,622,980 | B2 | 9/2003 | Boucher et al. |
| 7,349,203 | B2 | 3/2008 | Jobs et al. |
| 7,458,555 | B2 | 12/2008 | Mastropaolo et al. |
| 7,730,565 | B1 | 6/2010 | Masson |
| 7,778,848 | B1 | 8/2010 | Reeves |
| 7,821,782 | B2 | 10/2010 | Doherty et al. |
| 7,861,985 | B2 | 1/2011 | Galvin |
| 7,967,137 | B2 | 6/2011 | Fulbrook et al. |
| 7,971,289 | B2 | 7/2011 | Payne et al. |
| 8,011,629 | B2 | 9/2011 | Herskovic |
| 8,020,829 | B1 | 9/2011 | Tamayori |
| 8,053,670 | B2 * | 11/2011 | Lin .......................... H02G 3/088 174/50 |
| 8,461,968 | B2 | 6/2013 | Ball et al. |
| 8,485,404 | B2 | 7/2013 | Monaco et al. |
| 8,499,384 | B2 | 8/2013 | Zerhusen |
| D692,439 | S | 10/2013 | Muhlenberg |
| 8,602,662 | B1 | 12/2013 | Mans |
| 8,607,388 | B1 | 12/2013 | Flanagan et al. |
| 8,650,682 | B2 | 2/2014 | Herman |
| 8,661,583 | B2 | 3/2014 | Chinn et al. |
| 8,727,804 | B2 | 5/2014 | McNeely et al. |
| 8,763,802 | B2 | 7/2014 | Ellis-Brown |
| 8,789,802 | B2 | 7/2014 | Springer et al. |
| 8,794,766 | B2 | 8/2014 | Listou |
| 8,867,198 | B2 | 10/2014 | Steele |
| 8,917,496 | B2 | 12/2014 | Richardson et al. |
| 8,944,826 | B1 | 2/2015 | Wilkolaski et al. |
| 8,994,776 | B2 | 3/2015 | Sutherland et al. |
| 9,038,971 | B1 | 5/2015 | Guthrie |
| 9,147,965 | B2 | 9/2015 | Lee |
| 9,243,839 | B2 | 1/2016 | Kim et al. |
| 9,286,441 | B2 | 3/2016 | Zerhusen et al. |
| 9,375,374 | B2 | 6/2016 | Herman et al. |
| 9,444,237 | B2 * | 9/2016 | Frojo ...................... H02G 3/30 |
| 9,463,126 | B2 | 10/2016 | Zerhusen et al. |
| D773,465 | S | 12/2016 | Palmer et al. |
| 9,573,686 | B2 | 2/2017 | Barth |
| 9,643,767 | B2 | 5/2017 | Ziemba |
| 9,680,518 | B2 | 6/2017 | Wojcik et al. |
| 9,743,357 | B2 | 8/2017 | Tabe |
| 9,824,815 | B2 | 11/2017 | Leabman et al. |
| 10,013,868 | B2 | 7/2018 | Cox et al. |
| 10,028,875 | B2 | 7/2018 | Hatch |
| 10,175,723 | B2 | 1/2019 | Weldon |
| 2001/0022719 | A1 | 9/2001 | Armitage et al. |
| 2004/0174107 | A1 | 9/2004 | O'Halloran et al. |
| 2005/0062380 | A1 | 3/2005 | Park et al. |
| 2009/0255292 | A1 | 10/2009 | Benz et al. |
| 2010/0064721 | A1 | 3/2010 | Shin et al. |
| 2010/0132122 | A1 | 6/2010 | Hollingshead |
| 2011/0210833 | A1 | 9/2011 | McNeely et al. |
| 2011/0214234 | A1 | 9/2011 | Herman |
| 2011/0290807 | A1 | 12/2011 | Calvillo et al. |
| 2012/0026684 | A1 | 2/2012 | Matthews |
| 2012/0215360 | A1 | 8/2012 | Zerhusen et al. |
| 2013/0093388 | A1 | 4/2013 | Partovi |
| 2013/0314866 | A1 | 11/2013 | Millman |
| 2015/0024611 | A1 | 1/2015 | Wilkolaski et al. |
| 2015/0351530 | A1 | 12/2015 | Udagawa et al. |
| 2016/0008197 | A1 | 1/2016 | Zerhusen et al. |
| 2016/0047594 | A1 | 2/2016 | Choo et al. |
| 2016/0128468 | A1 | 5/2016 | Lafleche et al. |
| 2016/0183393 | A1 | 6/2016 | Groom et al. |
| 2016/0190838 | A1 | 6/2016 | Webb |
| 2016/0228091 | A1 | 8/2016 | Chiang et al. |
| 2016/0324701 | A1 | 11/2016 | Cambridge et al. |
| 2017/0035295 | A1 | 2/2017 | Collins, Jr. et al. |
| 2017/0052581 | A1 | 2/2017 | Enzinna |
| 2018/0168900 | A1 | 6/2018 | Mcneely et al. |

FOREIGN PATENT DOCUMENTS

| | | |
|---|---|---|
| EP | 2575263 | 4/2013 |
| KR | 20130004443 | 7/2013 |
| KR | 20170035851 | 3/2017 |
| WO | 2016155691 | 12/2016 |
| WO | 2016196403 | 12/2016 |
| WO | 2017131796 | 8/2017 |

OTHER PUBLICATIONS

"REGO Patient Interaction System," Curbell Medical, Online Available at https://curbellmedical.com/rego-ecosystem/, 8 pages.
U.S. Appl. No. 15/705,105, "Non Final Office Action", dated Nov. 14, 2017, 6 Pages.
U.S. Appl. No. 15/705,105, "Notice of Allowance", dated Mar. 27, 2018, 5 pages.
"2014 Manufacturers' Excellence Awards Finalists", Crestron Pyng™, Available Online at: http://cedia.net/programs/awards/winners/2014-manufacturers%27-excellence-awards-fina . . . , Accessed from Internet on Jul. 29, 2019, 15 pages.
"Announcing New Savant Home Automation Partners: Nest and iPort", INC, Available Online at: https://inctech.net/savant-announces-new-home-automation-partners/, Sep. 20, 2016, 2 pages.
"IPort® Announces The xPRESSTM Audio Keypad for Sonos®: Direct WiFi Control for Any Sonos Device", Available Online at: https://www.prnewswire.com/news-releases/iport-announces-the-xpress-audio-keypad-for-sonos-direct-wifi-control-for-any-sonos-device-300320239.h . . . , Aug. 30, 2016, 3 pages.
"Medical-Grade Tablet Cases Beat Pathogens", Maximise Technology, Available online at: https://www.maximisetechnology.com.au/medical-grade-device-cases-beat-pathogens-for-health-care/, 2019, 4 pages.
"Roomie Remote Launches 3.0 App for Home Theater and Home Automation at a Fraction of the Cost of Traditional Touch Panel Systems", Available Online at: https://dialog.proquest.com/professional/printviewfile?accountid=157769, Sep. 30, 2014, 2 pages.
"Savant Home Automation Works with Nest and iPort, Integrates Deeper with Sonos, PureLink", Available Online at: https://www.cepro.com/article/savant_home_automation_works_with_nest_iport_integrates_deeper_with_sonos, Sep. 27, 2016, 2 pages.

(56) References Cited

OTHER PUBLICATIONS

"SVI Trade Awards 2017—The Winners!", Available Online at: https://wws.v.svimag.com/news/svi_trade_awards_2017_the_winners, Apr. 27, 2017, 5 pages.

* cited by examiner

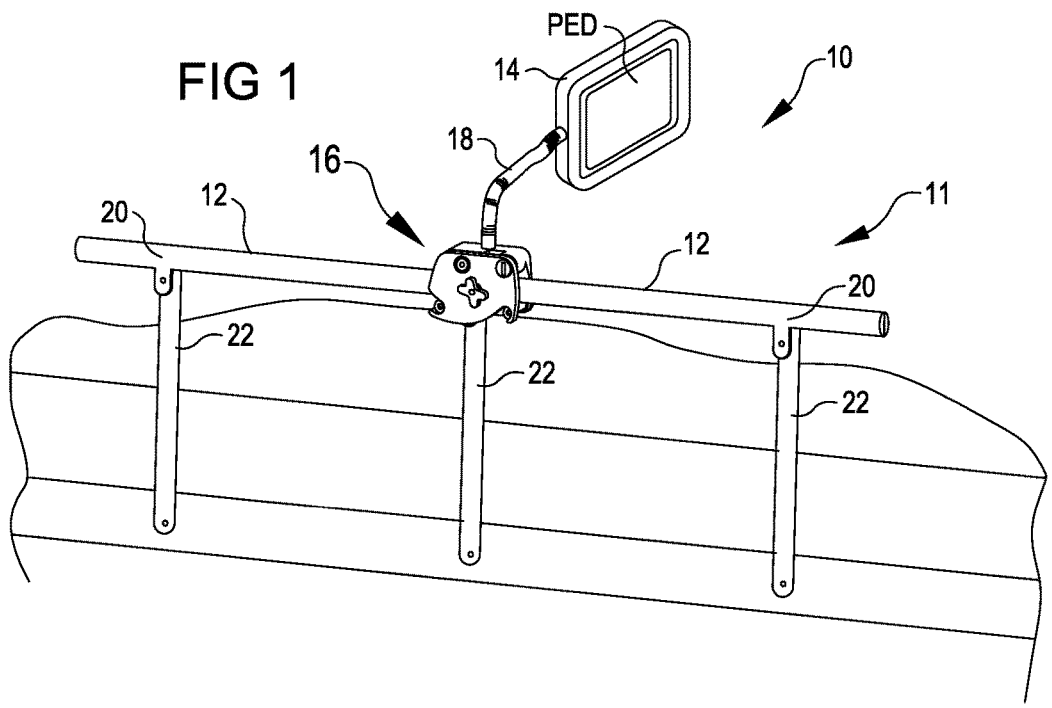
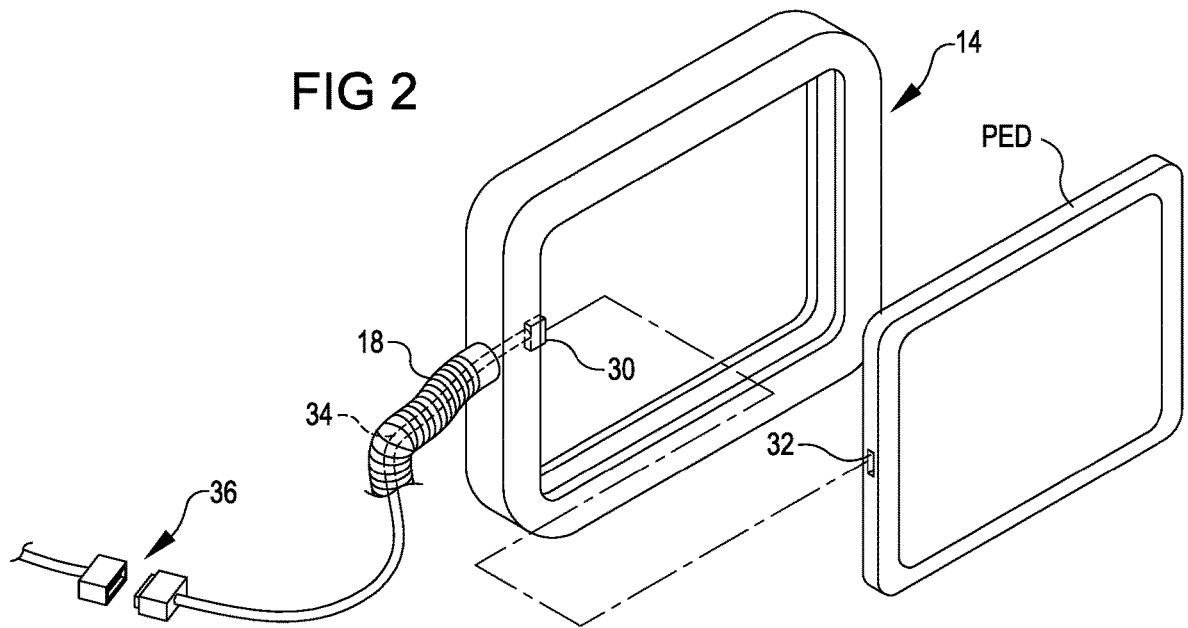

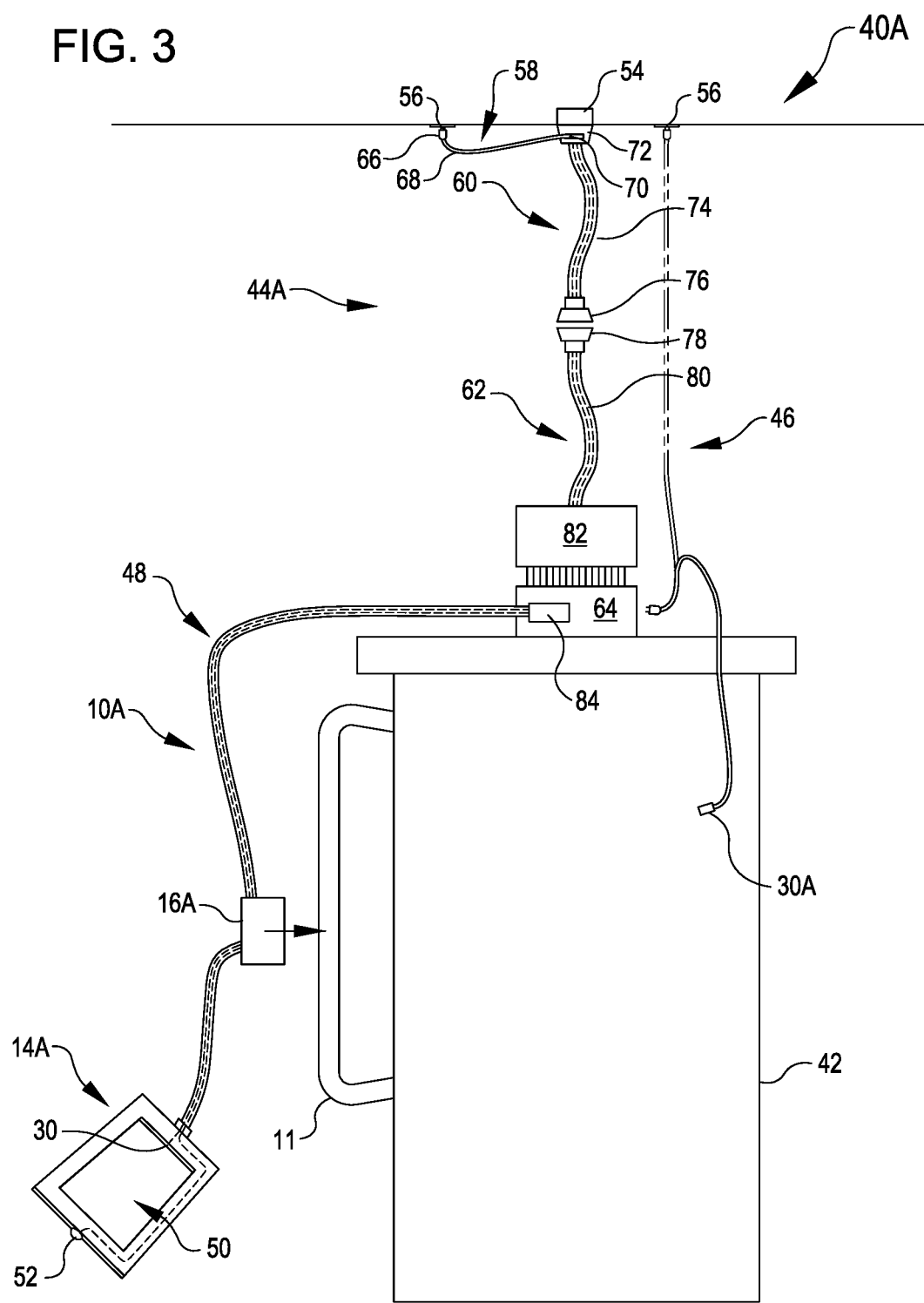

PORTABLE ELECTRONIC DEVICE HOLDER WITH ASSISTANCE REQUEST BUTTON AND METHOD POWERING PORTABLE ELECTRONIC DEVICE

CROSS-REFERENCES TO RELATED APPLICATIONS

This application claims the benefit of U.S. Provisional Application No. 62/567,670, filed Oct. 3, 2017, the entire contents of which are hereby incorporated for all purposes in its entirety.

BACKGROUND

Portable electronic devices (PEDs) (e.g., digital tablets, smart phones, and other electronic devices) are becoming more popular and prevalent in modern day lifestyles. Hospitals are experiencing increased usage of PEDs, either by patients and/or by hospital personnel. PEDs are being used in hospitals for communication, education, video conferencing with a patient who is in a hospital bed, and entertainment of the patient.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments herein are directed to portable electronic device (PED) related assemblies that are employable in a hospital room, may be integrated with existing assistance request systems, and can support the use of a PED by a patient in a hospital bed. In some embodiments, a PED related assembly includes one or more communication, data, and/or power cable assemblies that can be readily disconnected to accommodate movement of the hospital bed. In some embodiments, a PED related assembly includes a PED holder with an assistance request button and an output connector that is connectable to an input port of a PED held in the PED holder. As a result, a PED can be supplied power and/or data via a connection that enables use of the PED and the assistance request button by the patient, without compromising the ability to move the hospital bed.

Thus, in one aspect, a portable electronic device (PED) holder assembly includes a PED holder, an output connector, an assistance request button, a connection cable assembly, and a bed-side connector assembly. A PED is detachably attachable to the PED holder. The output connector is adapted for connection to an input port of a PED held to the PED holder. The assistance request button is attached to the PED holder. The connection cable assembly is operatively connected to the output connector and the assistance request button. The bed-side connector assembly is adapted to be connected to a bed-side end of a multifunctional assistance request cable. The bed-side connector assembly is operatively connected to the output connector, via the connection cable assembly, to transmit power received from the multifunctional assistance request cable to the PED. The bed-side connector assembly is operatively connected to the assistance request button to transmit an assistance request signal generated via a pressing of the assistance request button through the multifunctional assistance request cable to communicate a request for assistance.

In some embodiments, the bed-side connector assembly is configured for quick disconnection. For example, in some embodiments, the bed-side connector assembly includes a magnetic mechanism for detachably connecting the bed-side connector assembly to the bed-side end of the multifunctional assistance request cable.

In some embodiments, the bed-side connector assembly includes separate connectors through which power is supplied from the multifunctional assistance request cable to the PED and through which the assistant request signal is transmitted to the multifunction assistance request cable, respectively. For example, in some embodiments, the bed-side connector assembly includes a bed-side connector adapted to be connected to the bed-side end of the multifunctional assistance request cable. The bed-side connector can include a bed-side PED connector and a bed-side assistance request signal communication connector. The bed-side PED connector can be operatively connected to the output connector to transmit power received from the multifunctional assistance request cable to the PED. The bed-side assistance request signal communication connector can be connected to the assistance request button to transmit the assistance request signal through the multifunctional assistance request cable.

In some embodiments, the PED holder assembly further includes a wall-side connector assembly adapted to be connected to a wall-side end of the multifunctional assistance request cable. The wall-side connector assembly can be adapted to operatively connect a power source to the multifunctional assistance request cable to transmit power received from the power source to the PED via the multifunctional assistance request cable. The wall-side connector assembly can be adapted to connect the multifunctional assistance request cable to an assistance request communication system for transmission of the assistance request signal to the assistance request communication system to communicate the request for assistance.

In some embodiments, the wall-side connector assembly is configured for quick disconnection. For example, in some embodiments, the wall-side connector assembly includes a magnetic mechanism for detachably connecting the wall-side connector assembly to the wall-side end of the multifunctional assistance request cable.

In some embodiments, the wall-side connector assembly includes separate connectors through which power is transmitted through the multifunctional assistance request cable to the PED and through which the assistant request signal is transmitted from the multifunction assistance request cable to the assistance request communication system, respectively. For example, in some embodiments, the wall-side connector assembly includes a wall-side connector adapted to be connected to the wall-side end of the multifunctional assistance request cable. The wall-side connector can include a wall-side PED connector and a wall-side assistance request signal communication connector. The wall-side PED connector can be adapted to be connected to the power source to transmit power through the multifunctional assistance request cable to the PED. The wall-side assistance request signal communication connector can be adapted to be operatively connected to the assistance request communication system to transmit the assistance request signal from the multifunctional assistance request cable to the assistance request communication system.

In some embodiments, the PED holder assembly further includes the multifunctional assistance request cable. In some embodiments, the multifunctional assistance request cable is configured for quick disconnection. For example, the multifunctional assistance request cable can include a bed-side segment connected to the bed-side connector assembly, a wall-side segment connected to the wall-side connector assembly, and a magnetic mechanism for detachably connecting the bed-side segment to the wall-side segment.

In some embodiments, the assistance request button is illuminated when the PED holder assembly is connected to the power supply. For example, in some embodiments, the assistance request button includes an illumination element that outputs light when power received from the multifunctional assistance request cable is transmitted to the PED via the connection cable assembly. The illumination element does not output light when power is not transmitted to the PED via the connection cable assembly.

In some embodiments, the PED holder assembly includes a bed connector for keeping the PED holder assembly within easy reach of a patient in the hospital bed. For example, the bed connector can be adapted to attach to a side rail of a hospital bed and maintain a selected position of the connection cable assembly relative to the hospital bed.

In some embodiments, the PED holder assembly includes one or more additional assistance request buttons. Each of the one or more additional assistance buttons can be operatively connected to the connection cable assembly and operable to transmit an assistance request signal through the multifunctional assistance request cable to communicate a request for assistance.

In many embodiments, the PED holder assembly is configured to satisfy applicable safety regulations. For example, in many embodiments, the power transmitted to the PED via the multifunctional assistance request cable is National Fire Protection Association (NFPA) 99-compliant.

In many embodiments, the PED holder assembly is configured to transmit a signal to a PED held in the PED holder when the assistance request button is pressed. For example, the assistance request button can be operatively connected to the output connector to transmit an input signal to the PED indicative of a pressing of the assistance request button. The PED can be programmed to execute an assistance request program via which a request for assistance can be communicated via the PED.

In another aspect, a method is provided for transmitting power to a portable electronic device (PED) over a multifunctional assistance request cable and a request for assistance signal over the multifunctional assistance request cable. The method includes transmitting an electrical power from a power source to a multifunctional assistance request cable operatively connected to a hospital bed. The electrical power is transmitted from the multifunctional assistance request cable to an output connector. The electrical power is transmitted from the output connector to an input port of the PED detachably held in a PED holder. An assistance request signal is generated via a pressing of an assistance request button attached to the PED holder. The assistance request signal is transmitted, via the multifunctional assistance request cable, to an assistance request communication system to communicate an assistance request to an attendant.

In some embodiments, the method employs a wall-side connector assembly and/or a bed-side connector assembly through which the electrical power and the assistance request signal are transmitted. For example, the transmission of the electrical power from the power source to the multifunctional assistance request cable can include transmitting the electrical power from the power source to a PED connector of a wall-side connector assembly and transmitting the electrical power from the wall-side connector assembly to a wall-side end of the multifunctional assistance request cable. The transmission of the electrical power from the multifunctional assistance request cable to the output connector can include transmitting the electrical power from the multifunctional assistance request cable to a wall-side connector assembly connected to a bed-side end of the multifunctional assistance request cable and transmitting the electrical power from a PED connector of the wall-side connector assembly to the output connector. The transmission of the assistance request signal to the assistance request communication system can include transmitting the assistance request signal from the assistance request button to an assistance request signal connector of the bed-side connector assembly, transmitting the assistance request signal from the bed-side connector assembly to the multifunctional assistance request cable, transmitting the assistance request signal from the multifunctional assistance request cable to the wall-side connector assembly, and transmitting the assistance request signal from a wall-side assistance request signal connector of the wall-side connector assembly to the assistance request communication system.

In some embodiments, the method includes illumination of the assistance request button to indicate when power is being transmitted to the PED. For example, in some embodiments, the assistance request button includes an illumination element and the method further includes outputting light from the illumination element when power received from the multifunctional assistance request cable is transmitted to the input port of the PED and preventing output of light from the illumination element when power is not transmitted from the multifunctional assistance request cable to the input port of the PED.

In some embodiments, the method includes transmitting a signal to the PED indicative of a pressing of the assistance request button. For example, the assistance request button can be operatively connected to the output connector to transmit an input signal to the PED indicative of a pressing of the assistance request button. The PED can be programmed to execute an assistance request program via which a request for assistance can be generated and communicated via the PED.

In some embodiments of the method, the electrical power and the assistance request signal are transmitted through a magnetic connection assembly that includes a magnetic mechanism for detachably connecting the magnetic connection assembly. For example, the multifunctional assistance request cable can include a bed-side segment connected to the bed-side connector assembly, a wall-side segment connected to the wall-side connector assembly, and a magnetic mechanism for detachably connecting the bed-side segment to the wall-side segment. In some embodiments, the wall-side connector assembly includes a magnetic mechanism for detachably connecting the wall-side connector assembly to the wall-side end of the multifunctional assistance request cable. In some embodiments, the bed-side connector assembly includes a magnetic mechanism for detachably connecting the bed-side connector assembly to the bed-side end of the multifunctional assistance request cable For a fuller understanding of the nature and advantages of the present invention, reference should be made to the ensuing detailed description and accompanying drawings.

BRIEF DESCRIPTION OF THE DRAWINGS

The specification makes reference to the following appended figures, in which use of like reference numerals in different figures is intended to illustrate like or analogous components.

FIG. 1 shows a portable electronic device (PED) holder assembly that includes a bed connector that attaches to a side rail of the patient bed, in accordance with embodiments.

FIG. 2 shows some components of the PED holder assembly of FIG. 1.

FIG. 3 shows a hospital room configuration in which a PED holder assembly is connected to a communication and power assembly for a patient bed, in accordance with embodiments.

DETAILED DESCRIPTION

Figure 4:
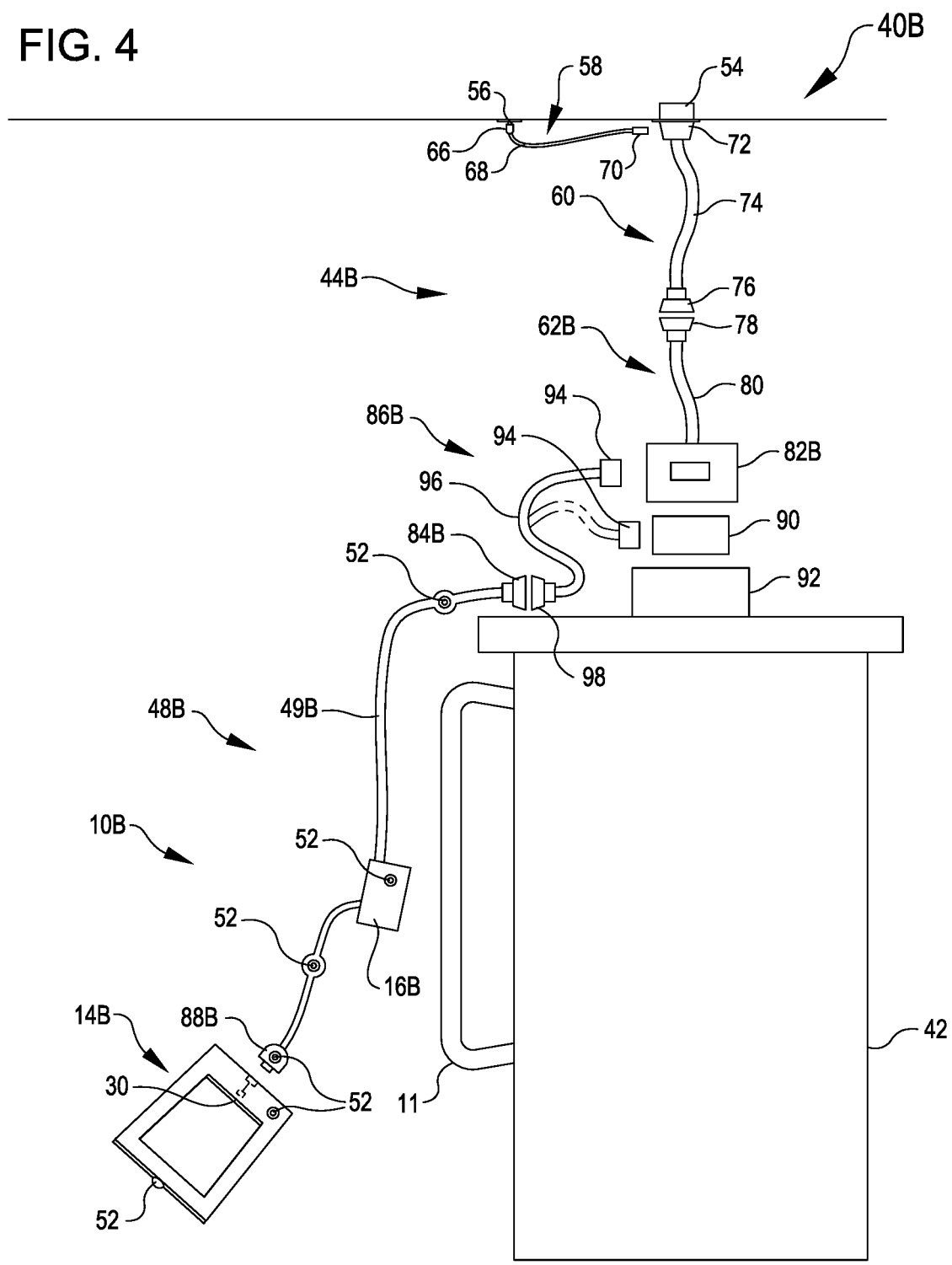
FIG. 4 shows a hospital room configuration in which a PED holder assembly is connected to a communication and power assembly for a patient bed, in accordance with embodiments, the PED holder assembly including one or more assistance request buttons.

In the following description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

As is known, a hospital bed or hospital stretcher is a patient holder assembly specially designed for hospitalized patients or others in need of some form of health care. As used herein throughout this disclosure, a "bed" refers to any patient holder assembly. Hospital beds have special features both for the comfort and well-being of the patient and for the convenience of health care workers. Common features include adjustable height for the entire bed, the head, and the feet, adjustable side rails, and electronic buttons to operate both the bed and other nearby electronic devices. Hospital beds and other similar types of beds are used not only in hospitals, but in other health care facilities and settings, such as nursing homes, assisted living facilities, outpatient clinics, and in home health care.

Many hospital beds have side rails that can be raised or lowered. These rails serve as protection for the patient and sometimes can make the patient feel more secure. There are a variety of different types of side rails designed to prevent falls, provide security for the patient, and/or provide assistance for the patient getting in and out of the bed. The side rails may or may not move with a head portion of the bed that moves upward to allow reclining by a patient.

Some embodiments herein are directed to a portable electronic device (PED) holder assembly that includes a bed connector releasably attaching the PED holder assembly to a bed side rail, for example for a hospital bed. In many embodiments, the bed connector is configured to releasably and securely mount to the side rail. In many embodiments, the PED holder assembly includes a support arm that is attached to the bed connector and to a PED holder to which a PED is attached. The support arm is, in embodiments, articulating, flexible, rotatable, and/or otherwise configurable to allow positioning of the PED holder in a desired position relative to the patient on the bed and/or hospital staff adjacent to the bed. The PED holder can be any structure that can support a PED. The PED can be any suitable portable electronic device, for example, a mobile phone, a smart phone, a personal digital assistant (PDA), a laptop computer, a desktop computer, a thin-client device, a tablet PC, an electronic book (e-book) reader, or other computing devices or electronic devices.

In some embodiments, the bed connector is designed to fit securely onto a side rail of a hospital bed so that the bed connector does not rotate relative to the side rail. In one such an embodiment, the bed connector can fit over the side rail and a bar that extends at an angle to the side rail, with the bed connector engaging both sides of the bar so that limited rotational movement of the bed connector is permitted after installation.

Turning now to the drawing figures in which the same or similar reference identifiers refer to the same or similar components throughout all of the drawing figures, FIG. 1 shows a PED holder assembly 10 for attaching a PED to hospital bed side rail 11. The PED holder assembly 10 includes a PED holder 14 to which the PED is attachable, a bed connector 16 for attaching to the bed side rail 11, and a support arm 18 extending between the bed connector 16 and the PED holder 14. In FIG. 1, the bed connector 16 is shown attached to a junction 20 at the top edge of a top rail 12 of the side rail 11 for a hospital bed. The junction 20 is the junction of the top rail 12 and a bar 22 that extends downward from the top rail 12. While suitable embodiments of the PED holder assembly 10 are described herein, U.S. patent application Ser. No. 15/705,105, entitled "Electronic Device Mount for Releasably Attaching to Equipment in a Hospital Room," which is hereby incorporated herein by reference in its entirety, provides description of a device 10 that is applicable to some embodiments of the PED holder assembly 10.

The PED holder 14 can be any suitable structure that can support a PED. For example, the PED holder 14 can include a device clamp that holds two or more sides of a PED, a stand that permits a PED to sit on top, a mount for supporting or holding a PED, one or more magnets for magnetically connecting to a PED, a tether, or any other structure that can clamp, friction fit, balance, suspend, or otherwise connect to or support a PED. The PED holder 14 can be designed to hold several different sized or shaped PEDs, and could be as simple as a flat surface. In many embodiments described herein, a PED holder assembly includes at least one assistance request button that can be pressed to communicate a request for assistance to an attendant station (e.g., a nurse station).

In some embodiments, the PED holder assembly 10 include an electrical connector for providing power and/or data to the PED. In embodiments, such electrical connector includes a charging feature for fitting into a charging port or otherwise connecting to the PED to provide power and/or data to the PED. For example, as shown by FIG. 2, the PED holder 14 can include a power and/or data output connector 30 for fitting into an input port 32 of the PED. The input port 32 of the PED can have any suitable configuration and be used to supply power to the PED and/or communicate data to and/or from the PED. For example, the power and/or data output connector 30 and the input port 32 can have any suitable Universal Serial Bus (USB) configuration. In some embodiments, the PED holder assembly 10 includes a battery, such as a rechargeable battery, for charging and/or powering the PED.

Power and/or data (e.g., data for communication) can be provided to the PED through the input port 32 via the power and/or data output connector 30. In such embodiments, a wire or set of wires can extend through the support arm 18, can be wrapped around the support arm 18, or can extend from the PED holder 14 free of the support arm 18. For example, as shown in FIG. 2, a cable 34 having one or more wires extends through the support arm 18. In embodiments, the PED holder assembly 10 includes a releasable connector 36, such as a magnetic connector disclosed in U.S. Pat. No. 9,147,965 (which is hereby incorporated herein in its entirety by reference), that can be disconnected so as to permit free movement of the portion of the PED holder assembly 10 connected to the hospital bed during movement of the hospital bed or when the PED holder assembly 10 is disconnected from the hospital bed. As an alternative to a wired connection, the PED can receive communications wirelessly, and the PED can be removed for charging or replacement of batteries. In addition, cable-less charging of the PED can be provided at the PED holder 14.

The support arm 18 is, in embodiments, articulating, flexible, rotatable, and/or otherwise configurable to allow positioning of the PED holder 14 in a desired position and orientation relative to the patient. In embodiments in which the support arm 18 is movable while the bed connector 16 remains anchored to the side rail 11, the support arm 18 and the PED holder 14 can be moved to a position out of the way in an emergency, but yet the PED holder 14 is still supported by the bed connector 16 via the side rail 11. In embodiments, the support arm 18 is not only reconfigurable to vary the position and/or orientation of the PED holder 14, but also retains the PED holder 14 in a selected position and orientation, such as over a patient or out to the side of a hospital bed for access by a caregiver. To this end, the support arm 18 can include sliding, locking pieces that accommodate repositioning and reorientation of the PED holder 14 and retain a selected position and orientation of the PED holder 14, or can have a flexible nature that resists, but allows, bending along its length. For example, the support arm 18 can include flexible adjustable shafts, such as those found in gooseneck lamps. As another example, the support arm 18 can include a coiled metal tube that is reconfigurable via selective bending along the length of the coiled metal tube.

FIG. 3 shows a hospital room configuration 40A that includes a hospital bed 42 having a side rail 11, a communication and power assembly 44A for the hospital bed 42, a PED holder assembly 10A, and, in some embodiments, a PED power and/or data cable assembly 46. The PED holder assembly 10A is configured similar to the PED holder assembly 10. For example, reference identifiers associated with components of PED holder assembly 10A that are the same or similar to components of the PED holder assembly 10 are the same or similar to reference identifiers associated with the components of the PED holder assembly 10. The PED holder assembly 10A includes a PED holder 14A, a bed connector 16A, and a power and/or data cable assembly 48. The PED holder 14A has a recess 50 shaped and sized to accommodate and hold a PED placed in the recess 50. In some embodiments, the PED holder 14A includes suitable retention features that retain the PED in the recess 50 to prevent inadvertent detachment of the PED from the PED holder 14A and accommodate intentional removal of the PED from the PED holder 14A. The PED holder 14A includes a power and/or data output connector 30 for fitting into an input port 32 of a PED held by the PED holder 14A. The PED holder 14A further includes a assistance request button 52 that can be pressed to communicate a request for assistance to an attendant station. The power and/or data cable assembly 48 operatively connects the power and/or data output connector 30 to the communication and power assembly 44A. The bed connector 16A is attachable to the side rail 11. The bed connector 16A is attached to, or attachable to, the power and/or data cable assembly 48 to retain the power and/or data cable assembly 48 within reach of a patient in the bed 42. In some embodiments, the distal end of the cable assembly 48 is securely attached to the PED holder 14A so that the patient can grab and pull on the cable assembly 48 to bring the PED holder 14A within reach of the patient when the patient wants to use the PED and/or press the assistance request button 52 to request assistance. In some embodiments, the PED holder assembly 10A includes a support arm the same as, or similar to, the support arm 18 of the PED holder assembly 10 to support the PED holder 14A in a selected position and orientation relative to the bed connector 16A.

In some embodiments, the communication and power assembly 44A operatively connects the bed 42 to a assistance request communication system hub 54 and connects the PED holder assembly 10A to a power and/or data outlet 56. The assistance request communication system hub 54 is operatively connected to a assistance request communication system that is operable to transmit a assistance request signal generated via operation of the assistance request button 52 to an attendant station. The power and/or data outlet 56 supplies power and/or data to a PED held by the PED holder assembly 10A through the communication and power assembly 44A and the cable assembly 48. The communication and power assembly 44A includes a PED power and/or data cable assembly 58, a proximal cable assembly 60, a distal cable assembly 62, and an intermediate connector 64 mounted to the bed 42. The PED power and/or data cable assembly 58 includes a proximal connector 66, a power and/or data cable 68, and a distal connector 70. The proximal cable assembly 60 includes a proximal connector 72, a power/communication cable 74, and a distal connector 76. The distal cable assembly 62 includes a proximal connector 78, a power/communication cable 80, and a distal connector 82. The proximal connector 66 of the cable assembly 58 is connectable to the power and/or data outlet 56 and the distal connector 70 of the cable assembly 58 is connectable to the proximal connector 72 of the cable assembly 60 to operatively connect the communication and power assembly 44A to the power and/or data outlet 56. The proximal connector 72 of the cable assembly 60 is connectable to the hub 54 to operatively connect the communication and power assembly 44A to the assistance request communication system. The proximal connector 78 of the cable assembly 62 is connectable to the distal connector 76 of the cable assembly 60 to operatively connect the cable assembly 62 to the assistance request communication system and the outlet 56. The distal connector 82 of the cable assembly 62 is connectable to the intermediate connector 64 to operatively connect the intermediate connector 64 to the assistance request communication system and the power and/or data outlet 56. The power and/or data cable assembly 48 includes a proximal connector 84 that is connectable to the intermediate connector 64 to operatively connect the power and/or data cable assembly 48 to the assistance request communication system and the outlet 56.

In some embodiments, the communication and power assembly 44A operatively connects the intermediate connector 64 to the assistance request communication system hub 54 and the intermediate connector 64 is operatively connected to a power and/or data outlet 56 via the PED power and/or data cable assembly 46. In the illustrated embodiment, the PED power and/or data cable assembly 46 includes a distal power and/or data output connector 30A, which can be connected to an input port 32 of a PED to operatively connect the PED to the power and/or data outlet 56.

In some embodiments, the communication and power assembly 44A is configured to enable quick disconnection of the bed 42 from the assistance request communication system hub 54 and the power and/or data outlet 56 when the bed 42 needs to be moved. For example, the distal connector 76 and the proximal connector 78 can form a releasable magnetic connection, such as the magnetic connector disclosed in U.S. Pat. No. 9,147,965. As another example, the distal connector 82 and the intermediate connector 64 can form a releasable magnetic connection, such as the magnetic connector disclosed in U.S. Pat. No. 9,147,965.

FIG. 4 shows a hospital room configuration 40B that includes a hospital bed 42 having a side rail 11, a communication and power assembly 44B for the hospital bed 42, an intermediate connector assembly 86B, and a PED holder assembly 10B. The PED holder assembly 10B is configured similar to the PED holder assembly 10. For example, reference identifiers associated with components of PED holder assembly 10B that are the same or similar to components of the PED holder assembly 10 are the same or similar to reference identifiers associated with the components of the PED holder assembly 10. The PED holder assembly 10B includes a PED holder 14B, a bed connector 16B, and a power and/or data cable assembly 48B. The PED holder 14B has a recess 50 shaped and sized to accommodate and hold a PED placed in the recess 50. In some embodiments, the PED holder 14B includes suitable retention features that retain the PED in the recess 50 to prevent inadvertent detachment of the PED from the PED holder 14B and accommodate intentional removal of the PED from the PED holder 14B. The PED holder 14B includes a power and/or data output connector 30 for fitting into an input port 32 of a PED held by the PED holder 14B. The PED holder 14B can include any suitable number of assistance request buttons 52 that can be pressed to communicate a request for assistance to an attendant station. For example, in the illustrated embodiment, the PED holder 14B includes two assistance request buttons 52. The power and/or data cable assembly 48B operatively connects the power and/or data output connector 30 and the assistance request buttons 52 to the intermediate cable assembly 86B. The power and/or data cable assembly 48B can include any suitable number of assistance request buttons 52 that can be pressed to communicate a request for assistance to an attendant station. For example, in the illustrated embodiment, the power and/or data cable assembly 48B includes three assistance request buttons 52 distributed along the length of the power and/or data cable assembly 48B. The power and/or data cable assembly 48B includes a distal connector 88B that is connectable to the PED holder 14B to operatively couple the PED holder 14B to the power and/or data cable assembly 48B. In the illustrated embodiment, the distal connector 88B includes a assistance request buttons 52 that can be pressed to communicate a request for assistance to an attendant station. The bed connector 16B is attachable to the side rail 11. The bed connector 16B is attached to, or attachable to, the power and/or data cable assembly 48B to retain the power and/or data cable assembly 48B within reach of a patient in the bed 42 so that the patient can grab and pull on the cable assembly 48 to bring the PED holder 14B within reach of the patient when the patient wants to use the PED and/or press the assistance request button 52 to request assistance. In some embodiments, the PED holder assembly 10B includes a support arm the same as, or similar to, the support arm 18 of the PED holder assembly 10 to support the PED holder 14B in a selected position and orientation relative to the bed connector 16B.

The communication and power assembly 44B operatively connects the intermediate cable assembly 86B to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder assembly 10B through the communication and power assembly 44B, the intermediate cable assembly 86B, and the cable assembly 48B. The communication and power assembly 44B includes the PED power and/or data cable assembly 58, the proximal cable assembly 60, a distal cable assembly 62B, and a coupler 90. The distal cable assembly 62B includes the proximal connector 78, the power/communication cable 80, and a distal connector 82B. The proximal connector 66 of the cable assembly 58 is connectable to the outlet 56 and the distal connector 70 of the cable assembly 58 is connectable to the proximal connector 72 of the cable assembly 60 to operatively connect the communication and power assembly 44B to the power and/or data outlet 56. The proximal connector 72 of the cable assembly 60 is connectable to the assistance request hub 54 to operatively connect the communication and power assembly 44B to the assistance request communication system. The proximal connector 78 of the cable assembly 62B is connectable to the distal connector 76 of the cable assembly 60 to operatively connect the cable assembly 62B to the assistance request communication system and the outlet 56. The distal connector 82B of the cable assembly 62 is connectable to the coupler 90 to operatively connect the coupler 90 to the assistance request communication system and the outlet 56. The bed 42 includes a bed hub 92 to which the coupler 90 is connectable to operatively connect the bed hub 92 to the assistance request communication system and/or the outlet 56. In some embodiments, the bed 42 includes any suitable number of assistance request buttons 52 that are operatively coupled with the assistance request communication system via the bed hub 92.

The intermediate cable assembly 86B operatively connects the PED holder assembly 10B to the assistance request communication system hub 54 and the outlet 56. The intermediate cable assembly 86B includes a proximal connector 94, a cable 96 operatively connected to the proximal connector 94, and a distal connector 98 operatively connected to the cable 96. In some embodiments, the proximal connector 94 is connectable to the distal connector 82B to operatively connect the intermediate cable assembly 86 to the assistance request communication system and the outlet 56 via the communication and power assembly 44B. In some embodiments, the proximal connector 94 is connectable to the coupler 90 to operatively connect the intermediate cable assembly 86 to the assistance request communication system and the outlet 56 via the communication and power assembly 44B.

The cable assembly 48B operatively connects the PED holder 14B to the assistance request communication system hub 54 and the outlet 56. The cable assembly 48B includes a proximal connector 84B, a cable 49B operatively connected to the proximal connector 84B, and the distal connector 88B operatively connected to the cable 49B. The proximal connector 84B is connectable to the distal connector 98 to operatively connect the cable assembly 48B to the assistance request communication system and the outlet 56 via the intermediate cable assembly 86B and the communication and power assembly 44B.

The hospital room configuration 40B can include any suitable number of quick disconnection features that enhance the ability to move the bed 42 and/or the PED holder assembly 10B. For example, in some embodiments, the distal connector 76 and the proximal connector 78 form a quick release connection, such as the magnetic connector disclosed in U.S. Pat. No. 9,147,965. In some embodiments, the distal connector 98 and the proximal connector 84B form a quick release connection, such as the magnetic connector disclosed in U.S. Pat. No. 9,147,965.

Figure 5:
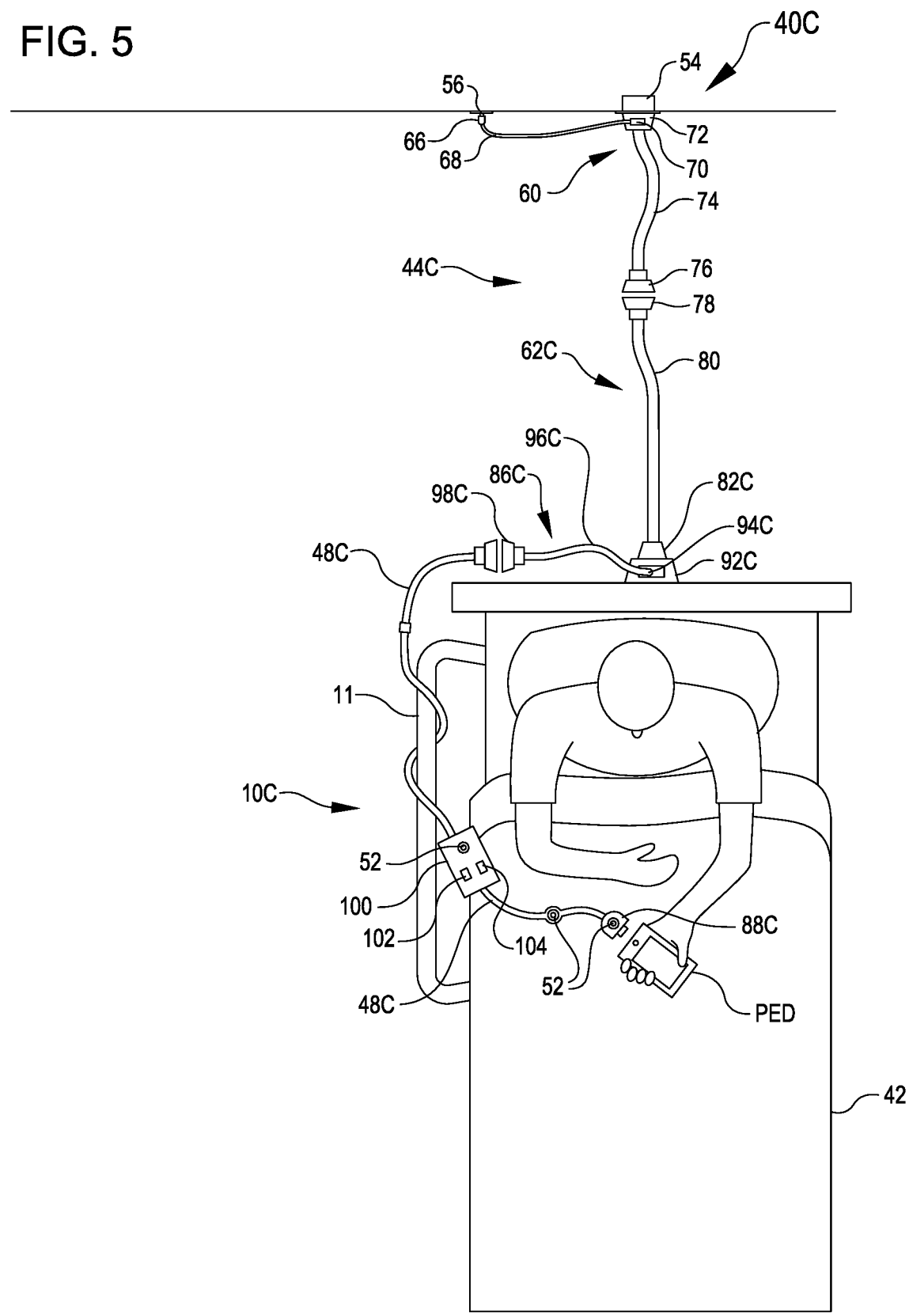
FIG. 5 shows a hospital room configuration in which a communication and power assembly for use by a patient is connected to a communication and power assembly for a patient bed, in accordance with embodiments.

FIG. 5 shows a hospital room configuration 40C that includes a hospital bed 42 having a side rail 11, a communication and power assembly 44C for the hospital bed 42, an intermediate connector assembly 86C, and a assistance request/PED cable assembly 10C. The assistance request/PED cable assembly 10C is configured similar to the PED holder assembly 10B, but without the PED holder 14B. For example, reference identifiers associated with components of assistance request/PED cable assembly 10C that are the same or similar to components of the PED holder assembly 10B are the same or similar to reference identifiers associated with the components of the PED holder assembly 10B. The assistance request/PED cable assembly 10C includes a proximal connector 84C, a cable assembly 48C, a patient interface unit 100, and a distal connector 88C. The distal connector 88C is a power and/or data output connector for fitting into an input port 32 of a PED. The distal connector 88C operatively connects the PED to the assistance request/PED cable assembly 10C. The cable assembly 48C can include any suitable number of assistance request buttons 52 that can be pressed to communicate a request for assistance to an attendant station. For example, in the illustrated embodiment, the cable assembly 48C includes one assistance request button located between the patient interface unit 100 and the distal connector 88C. The distal connector 88C also includes a assistance request buttons 52 that can be pressed to communicate a request for assistance to an attendant station. The patient interface unit 100 includes a assistance request button 52 and can include any suitable patient input devices, such as a remote control input devices for a television. In some embodiments, the cable assembly 48C can be wrapped around the side rail 11 to retain the cable assembly 48C within reach of a patient in the bed 42 when the patient wants to use the PED and/or press the assistance request button 52 to request assistance.

The communication and power assembly 44C operatively connects the intermediate cable assembly 86C to the assistance request communication system hub 54 and the outlet 56 and connects the bed 42 to the assistance request communication system hub 54 and, in some embodiments, the outlet 56. The power and/or data outlet 56 supplies power and/or data to a PED connected to the assistance request/PED cable assembly 10C through the communication and power assembly 44C, the intermediate cable assembly 86C, and the cable assembly 48C. The communication and power assembly 44C includes the PED power and/or data cable assembly 58, the proximal cable assembly 60, and a distal cable assembly 62C. The distal cable assembly 62C includes the proximal connector 78, the power/communication cable 80, and a distal connector 82C. The proximal connector 66 of the cable assembly 58 is connectable to the outlet 56 and the distal connector 70 of the cable assembly 58 is connectable to the proximal connector 72 of the cable assembly 60 to operatively connect the communication and power assembly 44C to the power and/or data outlet 56. The proximal connector 72 of the cable assembly 60 is connectable to the hub 54 to operatively connect the communication and power assembly 44C to the assistance request communication system. The proximal connector 78 of the cable assembly 62C is connectable to the distal connector 76 of the cable assembly 60 to operatively connect the cable assembly 62C to the assistance request communication system and the outlet 56. The bed 42 includes a bed hub 92C to which the distal connector 82C is connectable to operatively connect the bed hub 92C to the assistance request communication system and/or the outlet 56. In some embodiments, the bed 42 includes any suitable number of assistance request buttons 52 that are operatively coupled with the assistance request communication system via the bed hub 92C.

The intermediate cable assembly 86C operatively connects the assistance request/PED cable assembly 10C to the assistance request communication system hub 54 and the outlet 56 via the communication and power assembly 44C. The intermediate cable assembly 86C includes a proximal connector 94C, a cable 96C operatively connected to the proximal connector 94C, and a distal connector 98C operatively connected to the cable 96C. The proximal connector 94C is connectable to the bed hub 92C to operatively connect the intermediate cable assembly 86C to the assistance request communication system and the outlet 56 via the communication and power assembly 44C.

The hospital room configuration 40C can include any suitable number of quick disconnection features that enhance the ability to move the bed 42 and/or the assistance request/PED cable assembly 10C. For example, in some embodiments, the distal connector 76 and the proximal connector 78 form a quick release connection, such as the magnetic connector disclosed in U.S. Pat. No. 9,147,965. In some embodiments, the distal connector 98C and the proximal connector 84C form a quick release connection, such as the magnetic connector disclosed in U.S. Pat. No. 9,147,965.

Figure 6:
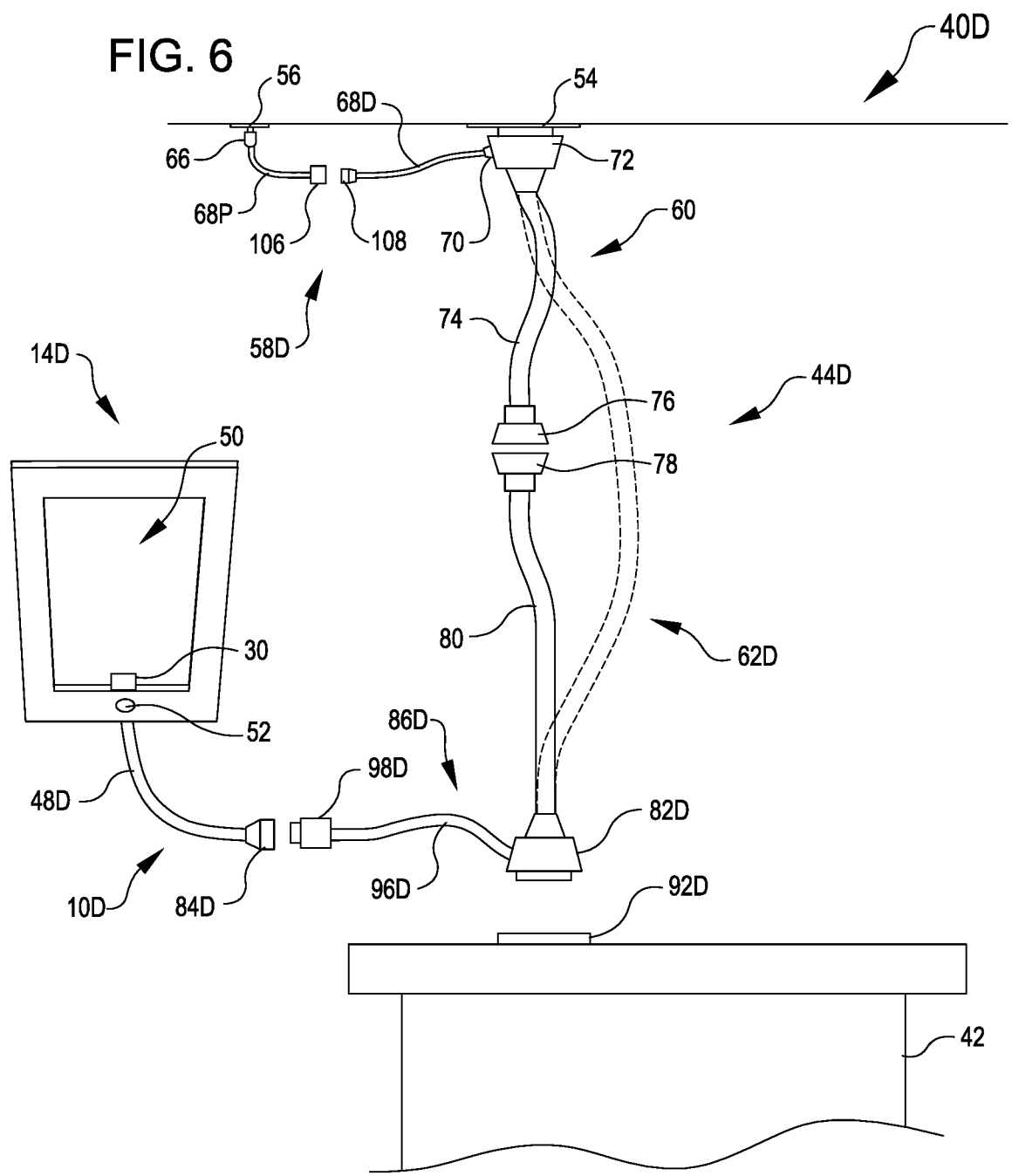
FIG. 6 shows a hospital room configuration in which a PED holder assembly is connected to a communication and power assembly for a patient bed, in accordance with embodiments, the PED holder assembly including a assistance request button.

FIG. 6 shows a hospital room configuration 40D that includes a hospital bed 42, a communication and power assembly 44D for the hospital bed 42, and a PED holder assembly 10D. The communication and power assembly 44D is configured similar to the communication and power assembly 44C, but including an intermediate connector assembly 86D that is integral to the distal cable assembly 62C. For example, reference identifiers associated with components of the communication and power assembly 44D that are the same or similar to components of the communication and power assembly 44C are the same or similar to reference identifiers associated with the components of the communication and power assembly 44C. The PED holder assembly 10D includes a proximal connector 84D, a cable assembly 48D, and a PED holder 14D. The PED holder assembly 10D is configured similar to the PED holder assembly 10. For example, reference identifiers associated with components of PED holder assembly 10D that are the same or similar to components of the PED holder assembly 10 are the same or similar to reference identifiers associated components of the PED holder assembly 10. The PED holder 14D can include any suitable number of assistance request buttons 52 that can be pressed to communicate a request for assistance to an attendant station. For example, in the illustrated embodiment, the PED holder 14D includes a single assistance request button 52.

The communication and power assembly 44D operatively connects the PED holder assembly 10D to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder 14D through the communication and power assembly 44D. The communication and power assembly 44D includes a PED power and/or data cable assembly 58D, the proximal cable assembly 60, and a distal cable assembly 62D. The distal cable assembly 62D includes the proximal connector 78, the power/communication cable 80, a distal connector 82D, and the intermediate connector assembly 86D. The PED power and/or data cable assembly 58D includes the proximal connector 66, a proximal cable 68P, a connector 106, a connector 108, a distal cable 68D, and the distal connector 70. The proximal connector 66 is connectable to the outlet 56, the connector 108 is connectable to the connector 106, and the distal connector 70 is connectable to the proximal connector 72 of the cable assembly 60 to operatively connect the communication and power assembly 44D to the power and/or data outlet 56. The proximal connector 72 of the cable assembly 60 is connectable to the assistance request hub 54 to operatively connect the communication and power assembly 44D to the assistance request communication system. The proximal connector 78 of the cable assembly 62D is connectable to the distal connector 76 of the cable assembly 60 to operatively connect the cable assembly 62D to the assistance request communication system and the outlet 56. The bed 42 includes a bed hub 92D to which the distal connector 82D is connectable to operatively connect the bed hub 92D to the assistance request communication system and/or the outlet 56. In some embodiments, the bed 42 includes any suitable number of assistance request buttons 52 that are operatively coupled with the assistance request communication system via the bed hub 92D. In some embodiments of the communication and power assembly 44D, the connectors 76, 78 are omitted and a single cable segment connects the connectors 72, 82D.

The intermediate cable assembly 86D operatively connects the PED holder assembly 10D to the assistance request communication system hub 54 and the outlet 56. The intermediate cable assembly 86C includes a cable 96D and a distal connector 98D operatively connected to the cable 96C. The cable 96D is operatively connected to the connector 82D and extends from the connector 82D.

The hospital room configuration 40D can include any suitable number of quick disconnection features that enhance the ability to move the bed 42 and/or the PED holder assembly 10D. For example, in some embodiments, the distal connector 76 and the proximal connector 78 form a quick release connection, such as the magnetic connector disclosed in U.S. Pat. No. 9,147,965. In some embodiments, the distal connector 98D and the proximal connector 84D form a quick release connection, such as the magnetic connector disclosed in U.S. Pat. No. 9,147,965.

Figure 7:
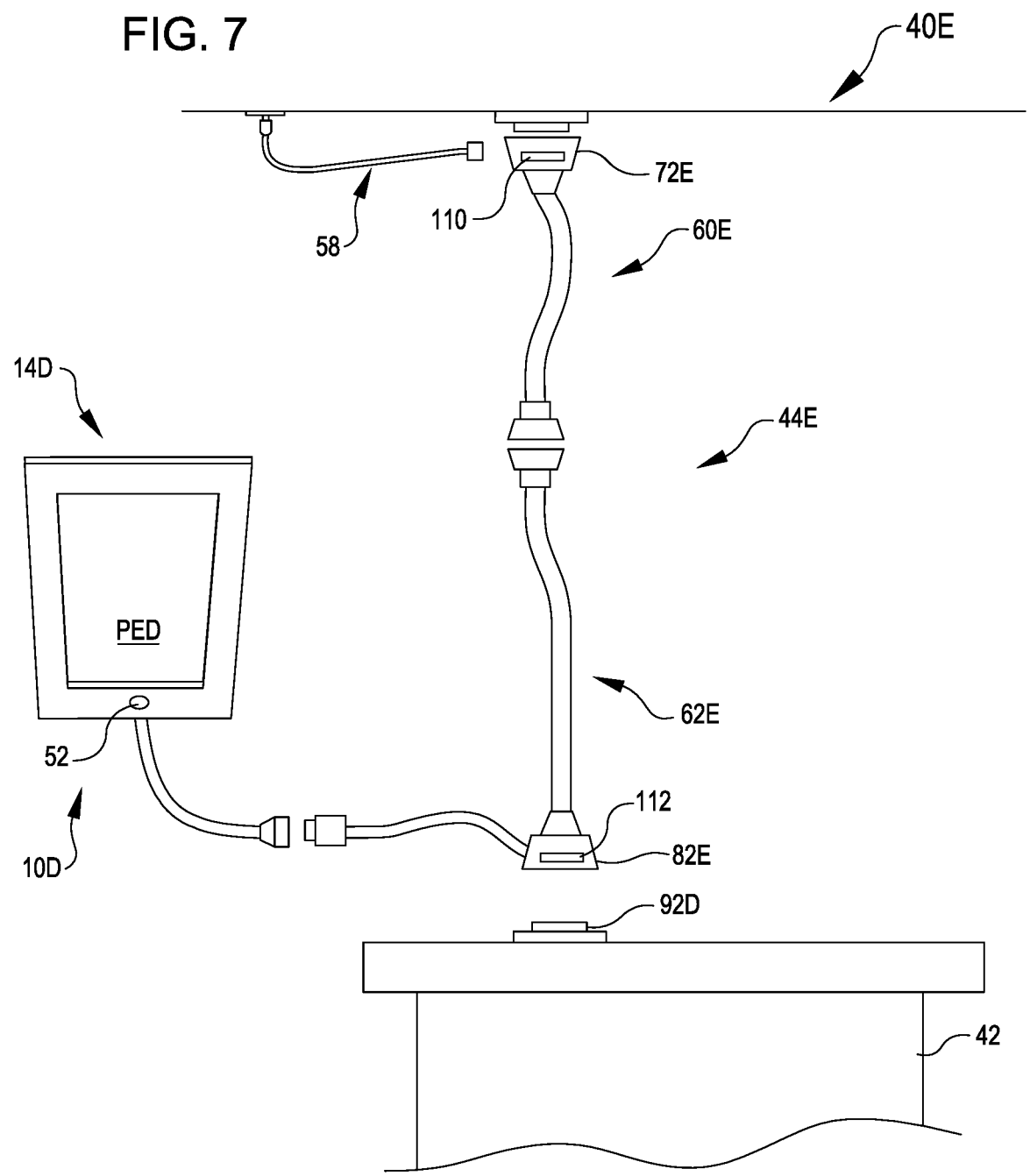
FIG. 7 shows a hospital room configuration in which a PED holder assembly is connected to a communication and power assembly for a patient bed, in accordance with embodiments, the PED holder assembly including a assistance request button.

FIG. 7 shows a hospital room configuration 40E that is similar to the hospital room configuration 40D except for differences described below. Reference identifiers associated with components of the hospital room configuration 40E that are the same or similar to components of the hospital room configuration 40D are the same or similar to reference identifiers associated with the components of the hospital room configuration 40D. The hospital room configuration 40E includes the one-piece PED power and/or data cable assembly 58 shown in FIG. 4 as opposed to the two-piece PED power and/or data cable assembly 58D shown in FIG. 6. The hospital room configuration 40E employs a communication and power assembly 44E as opposed to the communication and power assembly 44D shown in FIG. 6. The communication and power assembly 44E includes a proximal cable assembly 60E and a distal cable assembly 62E. The proximal cable assembly 60E is similar to the proximal cable assembly 60D, but has a proximal connector 72E that includes a power/data output port 110 to which a PED can be connected via a suitable connection cable. The distal cable assembly 62E is similar to the distal cable assembly 62E, but has a distal connector 82E that includes a power/data output port 112 to which a PED can be connected via a suitable connection cable.

Figure 8:
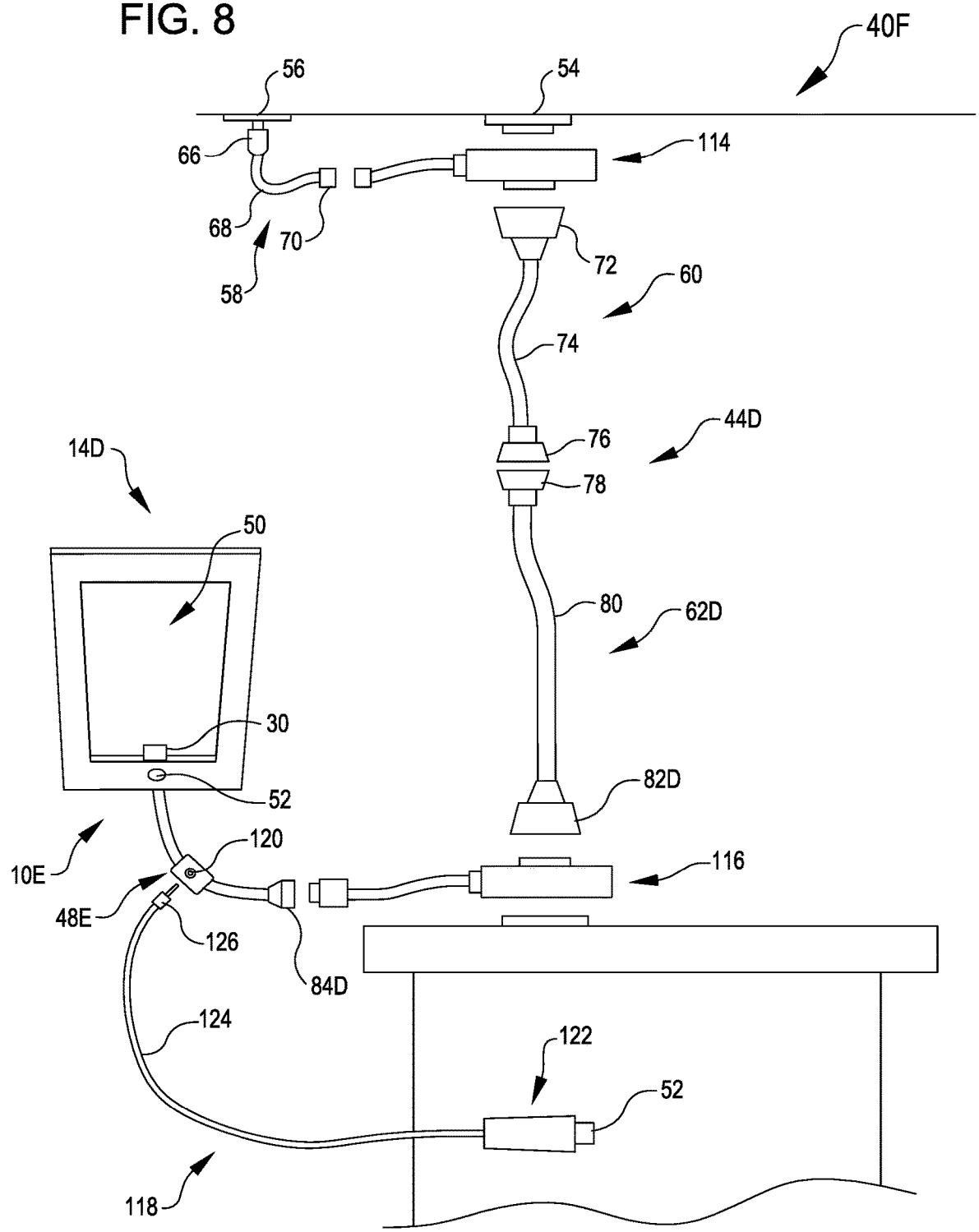
FIG. 8 shows a hospital room configuration in which a PED holder assembly is connected to a communication and power assembly for a patient bed, in accordance with embodiments, the PED holder assembly including a connection port for a assistance request button assembly.

FIG. 8 shows a hospital room configuration 40F that is similar to the hospital room configuration 40D except for differences described below. Reference identifiers associated with components of the hospital room configuration 40F that are the same or similar to components of the hospital room configuration 40D are the same or similar to reference identifiers associated with the components of the hospital room configuration 40D. The hospital room configuration 40F includes a proximal coupler 114 and a distal coupler 116. The proximal coupler 114 is connectable to and between the proximal connector 72 and the assistance request hub 54 to operatively couple the communication and power assembly 44D to the assistance request hub 54. Additionally, the proximal coupler 114 operatively couples the communication and power assembly 44D to the PED power and/or data cable assembly 58. The distal coupler 116 is connectable to and between the distal coupler 82D and the bed hub 92D to operatively coupled the bed 42 to the assistance request hub 54, and in some embodiments, to the power and/or data outlet 56. Additionally, the distal coupler 116 is connectable to and between the distal coupler 82D and the proximal connector 84D of the PED holder assembly 10E to operatively couple the PED holder assembly 10E to the assistance request hub 54 and the power and/or data outlet 56. The PED holder assembly 10E is configured similar to the PED holder assembly 10D shown in FIG. 6, but includes a assistance request cable assembly 118 and a connection port 120 to which the assistance request cable assembly 118 can be operatively connected to the assistance request hub 54. The assistance request cable assembly 118 includes a assistance request button assembly 122, a cable 124, and a proximal connector 126 connected to the assistance request button assembly 112 by the cable 124. The assistance request button assembly 122 includes a assistance request button 52 that can be pressed by a patient to communicate a request for assistance to an attendant station.

The hospital room configuration 40F can include any suitable number of quick disconnection features that enhance the ability to move the bed 42 and/or the PED holder assembly 10E. For example, in some embodiments, the distal connector 76 and the proximal connector 78 form a quick release connection, such as the magnetic connector disclosed in U.S. Pat. No. 9,147,965. In some embodiments, the proximal coupler 114 forms part of a quick release connection, such as the magnetic connector disclosed in U.S. Pat. No. 9,147,965. In some embodiments, the distal coupler 116 forms part of a quick release connection, such as the magnetic connector disclosed in U.S. Pat. No. 9,147,965.

Figure 9:
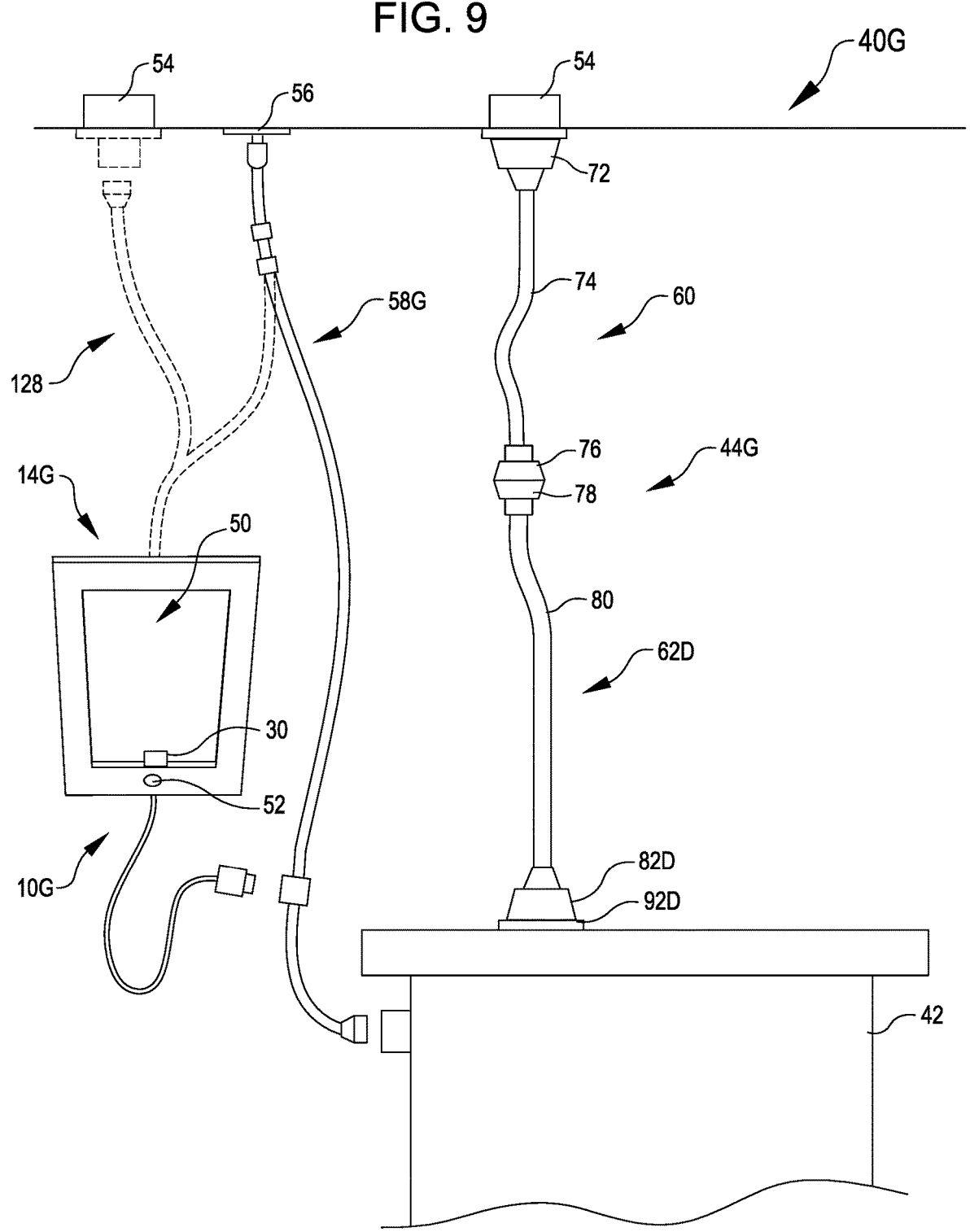
FIG. 9 shows a hospital room configuration that includes a PED holder assembly that can be connected to a communication and power assembly for a patient bed or connected directly to a power and/or data device that supplies power and/or data to a PED, in accordance with embodiments, the PED holder assembly including a assistance request button.

FIG. 9 shows a hospital room configuration 40G in which the bed 42 is coupled to the assistance request hub 54 via a assistance request communication cable assembly 44G. In some embodiments, the bed 42 is separately coupled to a power and/or data output 56 via a cable assembly 58G. The configuration 40G includes a PED holder assembly 10G, which in some embodiments is configured the same as the PED holder assembly 10D shown in FIG. 6 and be operatively connectable to the power and/or data output 56 through the cable assembly 58G and to the assistance request hub 54 through a communication path that includes the cable assembly 58G, the bed 42, and the assistance request communication cable assembly 44G. In an alternate embodiment, the PED holder assembly 10G includes a connection cable assembly 128 that operatively couples the PEG holder assembly 10G to a assistance request hub 54 and the power and/or data output 56.

Figure 10:
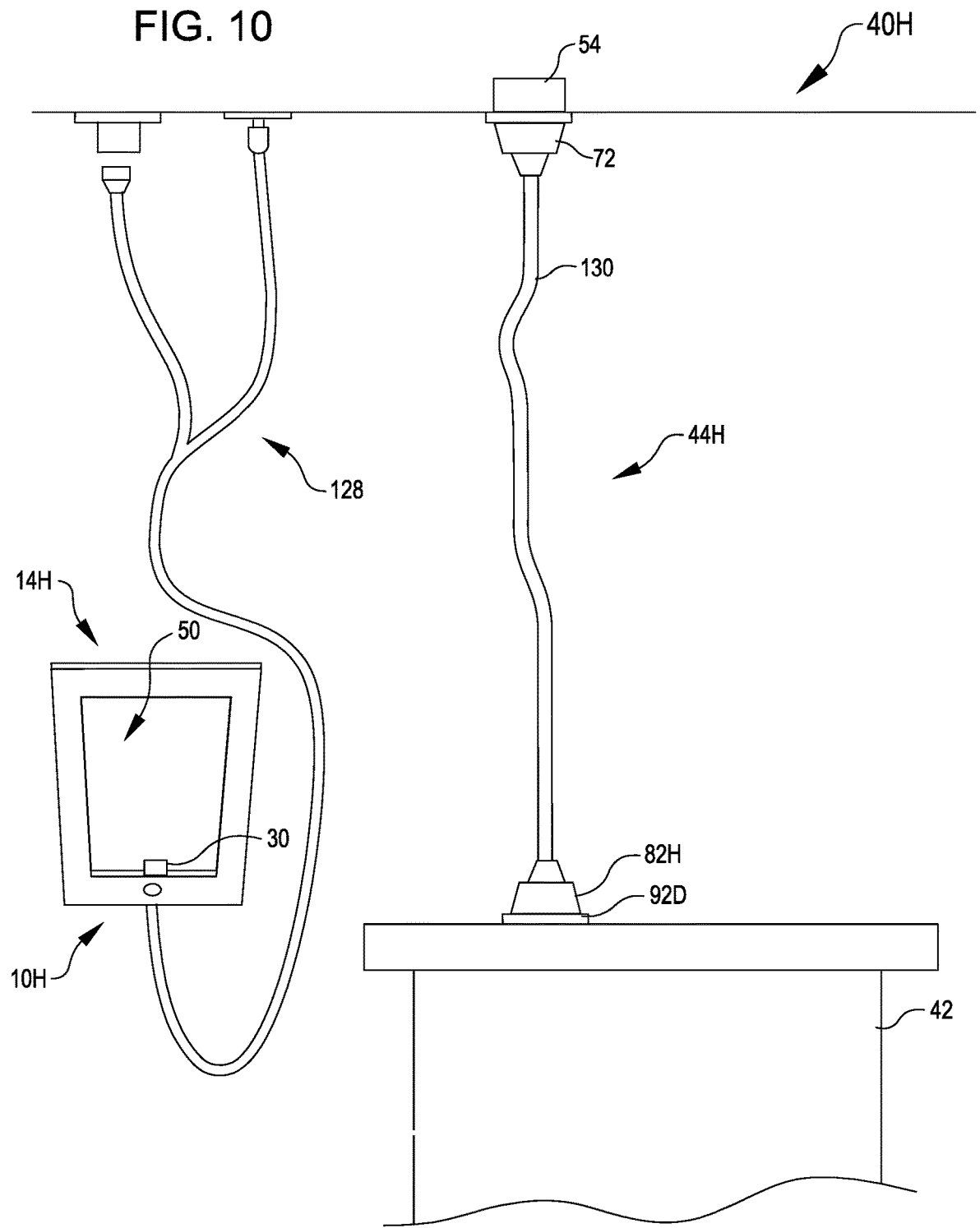
FIG. 10 shows a hospital room configuration that includes a PED holder assembly connected directly to a power and/or data device that supplies power and/or data to a PED, in accordance with embodiments, the PED holder assembly including a assistance request button.

FIG. 10 shows a hospital room configuration 40H that is similar to the hospital room configuration 40G shown in FIG. 9 except for differences described below. In the hospital room configuration 40H, the bed 42 is coupled to a assistance request hub 54 via a assistance request communication cable assembly 44H and a PED holder assembly 10H is coupled to a assistance request hub 54 and the power and/or data outlet 56 without being connected to the assistance request communication cable assembly 44H or the bed 42. The PED holder assembly 10H includes a PED holder 14H (which is configured similar to the PED holder 14D) and the connection cable assembly 128, which is connectable to each of a assistance request hub 54 and the power and/or data outlet 56 to operatively coupled the PED holder assembly 10H to the assistance request hub 54 and the power and/or data outlet 56. The hospital room configuration 40H can be implemented by adding the PED holder assembly 10H to an existing hospital room configuration that includes the bed 42 and the assistance request communication cable assembly 44H coupling the bed hub 92D to the assistance request hub 54. In the illustrated embodiment, the assistance request communication cable assembly 44H includes a single cable segment 130 that operatively connects the distal connector 82D to the proximal connector 72.

Figure 11:
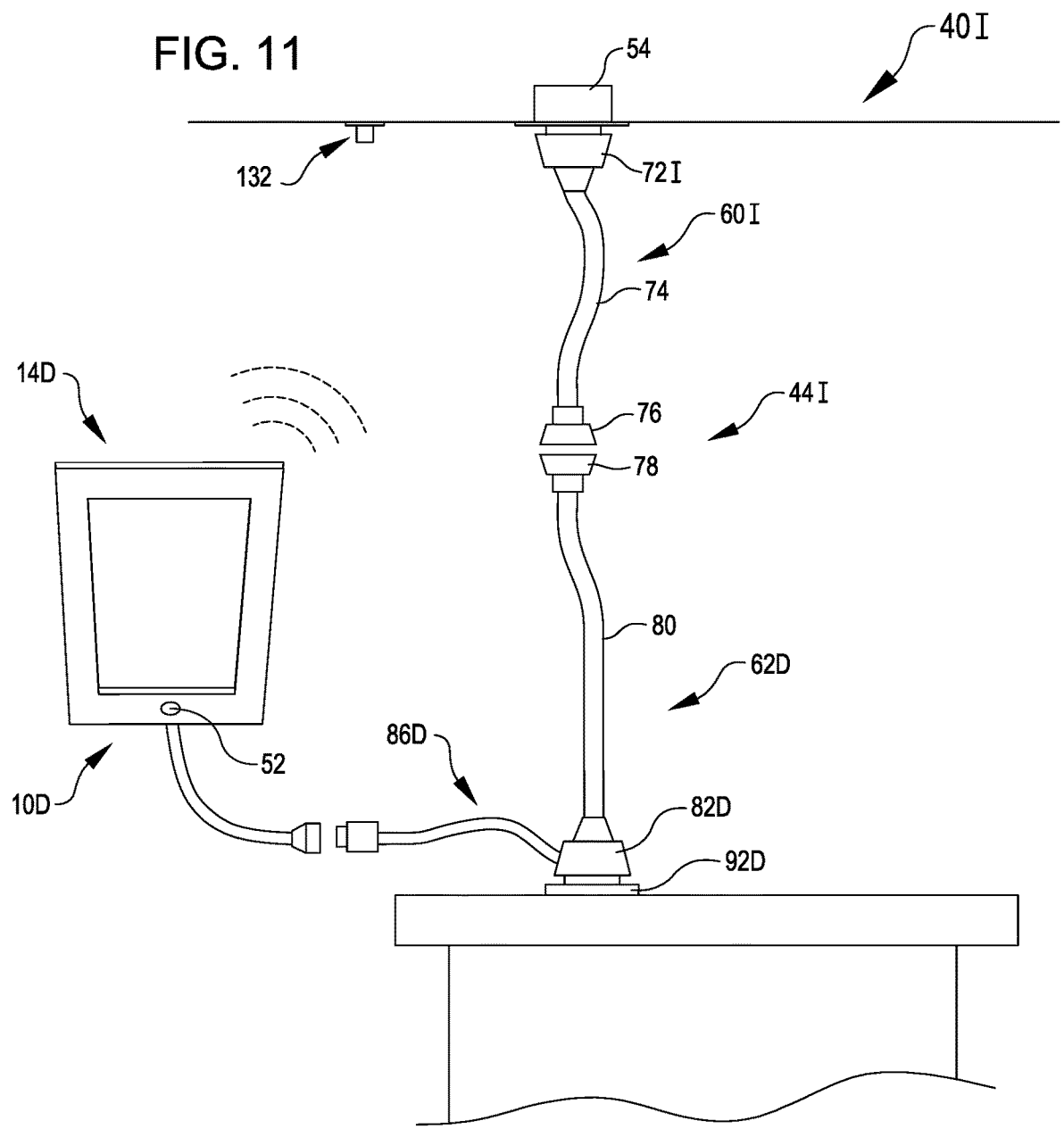
FIG. 11 shows a hospital room configuration in which a PED holder assembly is connected to a communication and power assembly for a patient bed, in accordance with embodiments, the PED holder assembly including a assistance request button and wireless communication functionality.

FIG. 11 shows a hospital room configuration 40*i* that is similar to the hospital room configuration 40E shown in FIG. 7 except for differences described below. The hospital room configuration 40*i* includes the PED holder assembly 10D and a assistance request communication cable assembly 44*i*. The assistance request communication cable assembly 44*i* is similar to the power and communication cable 44D shown in FIG. 6, but has a proximal cable assembly 60*i* that includes a proximal connector 72*i* that only connects to the assistance request hub 54 in contrast to the proximal connector 72 that connects to both the assistance request hub 54 and the power and/or data outlet 56 via the power and/or data cable assembly 58D as shown in FIG. 6. In the hospital room configuration 40*i*, the PED held by the PED holder 14D communicates wirelessly to a wireless router 132. The PED holder 14D can include a rechargeable battery that supplies power to recharge and/or operate the PED. In some embodiments, the PED holder assembly 10D supplies the PED with power transferred to the PED holder assembly 10D by the assistance request communication cable assembly 44*i*.

Figure 12:
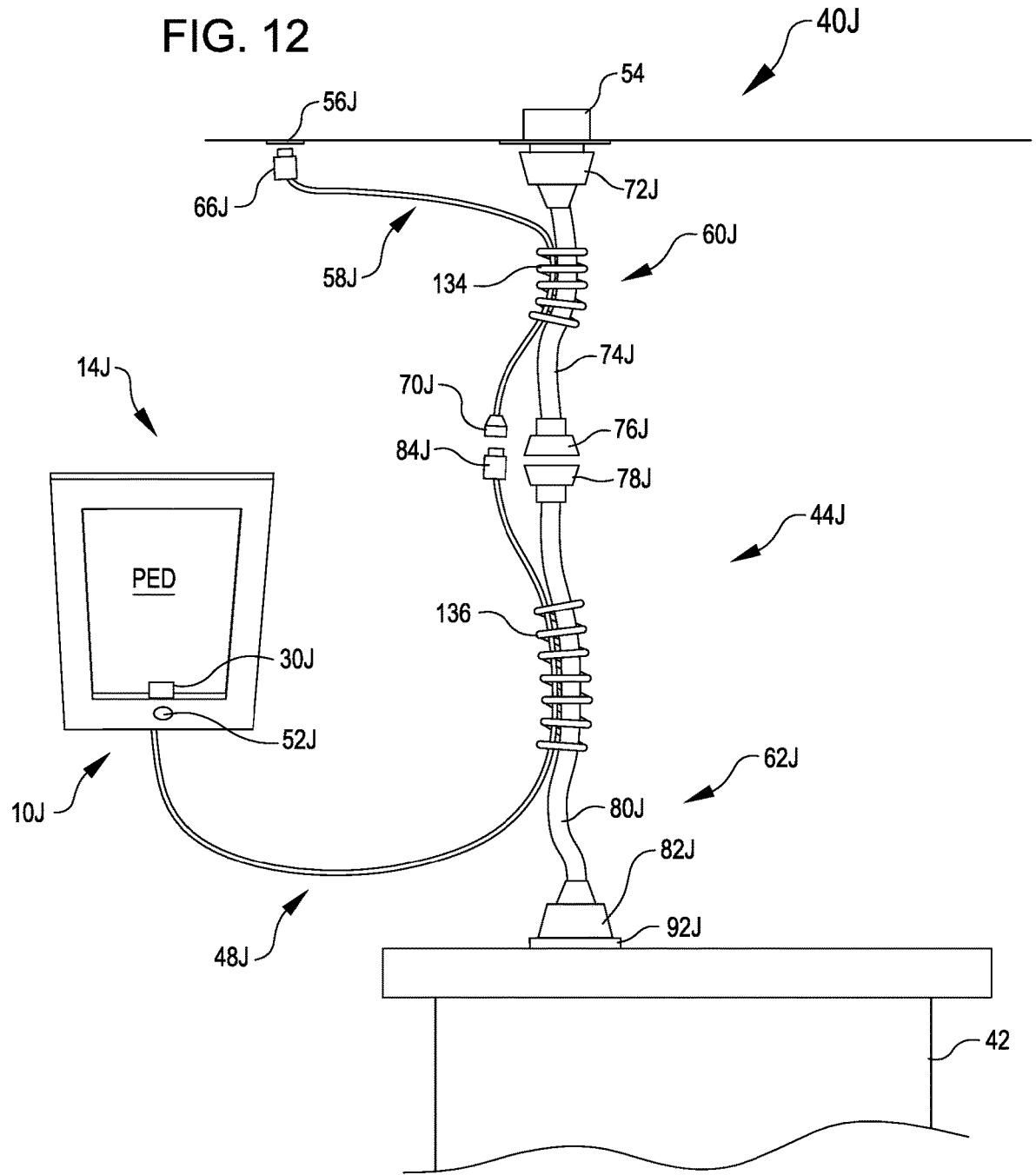
FIG. 12 shows a hospital room configuration that includes a PED holder assembly connected directly to a power and/or data device that supplies power and/or data to a PED, in accordance with embodiments, the PED holder assembly including a assistance request button and a connector disposed adjacent to a connector of a communication and power assembly for a patient bed.

FIG. 12 shows a hospital room configuration 40J that includes a PED holder assembly 10J, a power and data cable assembly 58J, a bed 42, and a assistance request communication cable assembly 44J. The PED holder assembly 10J includes a PED holder 14J and a power and data cable assembly 48J. The PED holder 14J includes a power and/or data output connector 30J for fitting into an input port 32 of a PED held by the PED holder 14J. The PED holder 14J further includes a assistance request button 52J that is operatively coupled to the connector 30J. The PED power and/or data cable assembly 58J includes a proximal connector 66J, a power and/or data cable 68J, and a distal connector 70J. The assistance request button 52J can be pressed to communicate a request for assistance to the PED held by the PED holder 30J. The power and data cable assembly 48J includes a proximal connector 84J that is connectable to the distal connector 70J to operatively connect the power and data cable assembly 48J to the outlet 56. The power and data cable assembly 48J operatively connects the power and/or data output connector 30 to a power and data outlet 56J via the power and data cable assembly 58J. In some embodiments, the PED held by the PED holder 14J, in response to receiving a request for assistance generated via pushing of the assistance request button 52J, transmits a request for assistance to an attendant station via the power and data outlet 56J. The assistance request communication cable assembly 44J includes a proximal cable assembly 60J and a distal cable assembly 62J. The proximal cable assembly 60J includes a proximal connector 72J, a communication cable 74J, and a distal connector 76J. The distal cable assembly 62J includes a proximal connector 78J, a communication cable 80J, and a distal connector 82J. The proximal connector 72J of the cable assembly 60J is connectable to the assistance request hub 54 to operatively connect the assistance request communication cable assembly 44J to the assistance request communication system. The proximal connector 78J of the cable assembly 62J is connectable to the distal connector 76J of the cable assembly 60J to operatively connect the cable assembly 62J to the assistance request communication system. The distal connector 82J of the cable assembly 62J is connectable to a bed connector 92J to operatively couple the bed 42 to the assistance request communication system.

In the illustrated embodiment, the distal cable assembly 62J is configured for quick disconnection from the proximal cable assembly 60J, and the power and data cable assembly 48J is configured for quick disconnection from the power and data cable assembly 58J, when the bed 42 needs to be moved. For example, the distal connector 76J and the proximal connector 78J can form a releasable magnetic connection, such as the magnetic connector disclosed in U.S. Pat. No. 9,147,965. As another example, the proximal connector 84J and the distal connector 70J can form a releasable magnetic connection, such as the magnetic connector disclosed in U.S. Pat. No. 9,147,965. In the illustrated embodiment, the proximal cable assembly 60J is coupled with the power and data cable assembly 58J via a proximal coupler 134, and the distal cable assembly 62J is coupled with the power and data cable assembly 48J via a distal coupler 136 so that the connectors 70J, 74J, 76J, 84J are held in close proximity to support quick disconnection of both connector 84J from connector 70J and connector 78J from connector 76J.

Figure 13:
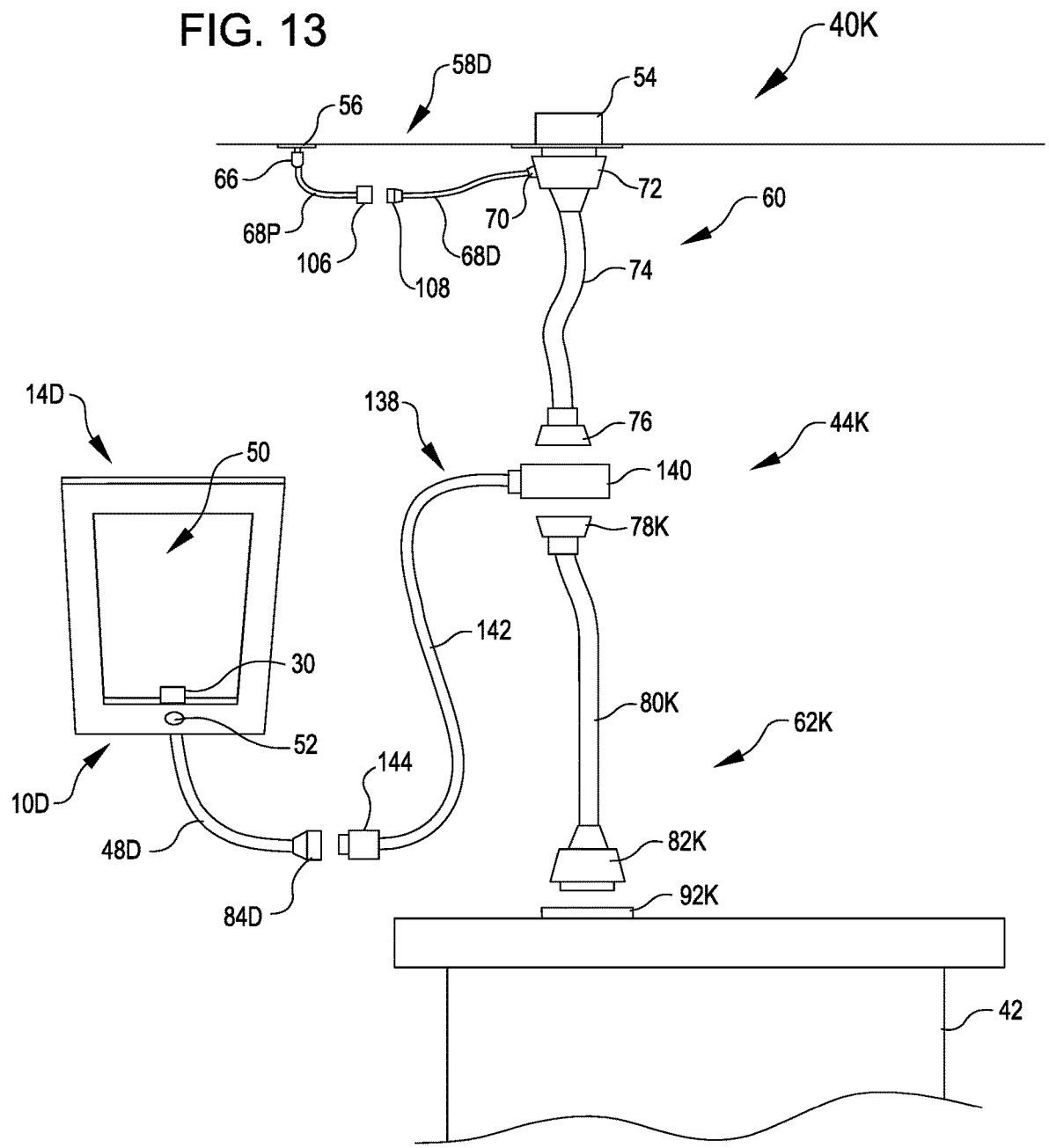
FIG. 13 shows a hospital room configuration in which a PED holder assembly is connected to a communication and power assembly for a patient bed, in accordance with embodiments, the PED holder assembly including a assistance request button.

FIG. 13 shows a hospital room configuration 40K that includes a hospital bed 42, a communication and power assembly 44K for the hospital bed 42, and the PED holder assembly 10D. The communication and power assembly 44K is configured similar to the communication and power assembly 44C, but including an intermediate coupler assembly 138. Reference identifiers associated with components of the communication and power assembly 44C that are the same or similar to components of the communication and power assembly 44K are the same or similar to reference identifiers associated with the components of the communication and power assembly 44K. The PED holder assembly 10D includes the proximal connector 84D, the cable assembly 48D, and the PED holder 14D. The PED holder 14D includes the power and/or data output connector 30 for fitting into an input port 32 of a PED held by the PED holder 14D. In the illustrated embodiment, the PED holder 14D includes a single assistance request button 52.

The communication and power assembly 44K operatively connects the PED holder assembly 10D to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder 14D through the communication and power assembly 44K. The communication and power assembly 44K includes the PED power and/or data cable assembly 58D, the proximal cable assembly 60, and a distal cable assembly 62K. The distal cable assembly 62k includes a proximal connector 78K, a assistance request communication cable 80K, and a distal connector 82K. The PED power and/or data cable assembly 58D includes the proximal connector 66, a proximal cable 68P, a connector 106, a connector 108, a distal cable 68D, and the distal connector 70. The proximal connector 66 is connectable to the outlet 56; the connector 108 is connectable to the connector 106; and the distal connector 70 is connectable to the proximal connector 72 of the cable assembly 60 to operatively connect the communication and power assembly 44K to the power and/or data outlet 56. The proximal connector 72 of the cable assembly 60 is connectable to the hub 54 to operatively connect the communication and power assembly 44K to the assistance request communication system. The proximal connector 78K of the cable assembly 62K is indirectly connectable, via the intermediate coupler assembly 138, to the distal connector 76 of the cable assembly 60 to operatively connect the cable assembly 62K to the assistance request communication system and, in some embodiments, to the outlet 56. The bed 42 includes a bed hub 92K to which the distal connector 82K is connectable to operatively connect the bed hub 92K to the assistance request communication system and, in some embodiments, to the outlet 56. In some embodiments, the bed 42 includes any suitable number of assistance request buttons 52 that are operatively coupled with the assistance request communication system via the bed hub 92K.

The intermediate coupler assembly 138 operatively connects the PED holder assembly 10D to the communication and power assembly 44K. The intermediate coupler assembly 138 includes a coupler 140, a cable 142, and a distal connector 144 operatively connected to the cable 142. The cable 142 is operatively connected to the coupler 140 and extends from the connector coupler 140. The coupler 140 is connectable to and between the distal connector 76 and the proximal connector 78K to operatively couple the cable assembly 62K and the intermediate coupler assembly 138 to the cable assembly 60 and, thereby, to the assistance request communication system and the outlet 56. The proximal connector 84D is connectable to the distal connector 144 to operatively coupled the PED holder assembly 10D to the communication and power assembly 44K and, thereby, to the assistance request communication system and the power and/or data outlet 56.

The hospital room configuration 40K can include any suitable number of quick disconnection features that enhance the ability to move the bed 42 and/or the PED holder assembly 10D. For example, in some embodiments, the distal connector 76 and the coupler 140 form a quick release connection, such as the magnetic connector disclosed in U.S. Pat. No. 9,147,965. In some embodiments, the coupler 140 and the proximal connector 78K form a quick release connection, such as the magnetic connector disclosed in U.S. Pat. No. 9,147,965. In some embodiments, the distal connector 144 and the proximal connector 84D form a quick release connection, such as the magnetic connector disclosed in U.S. Pat. No. 9,147,965.

Figure 14:
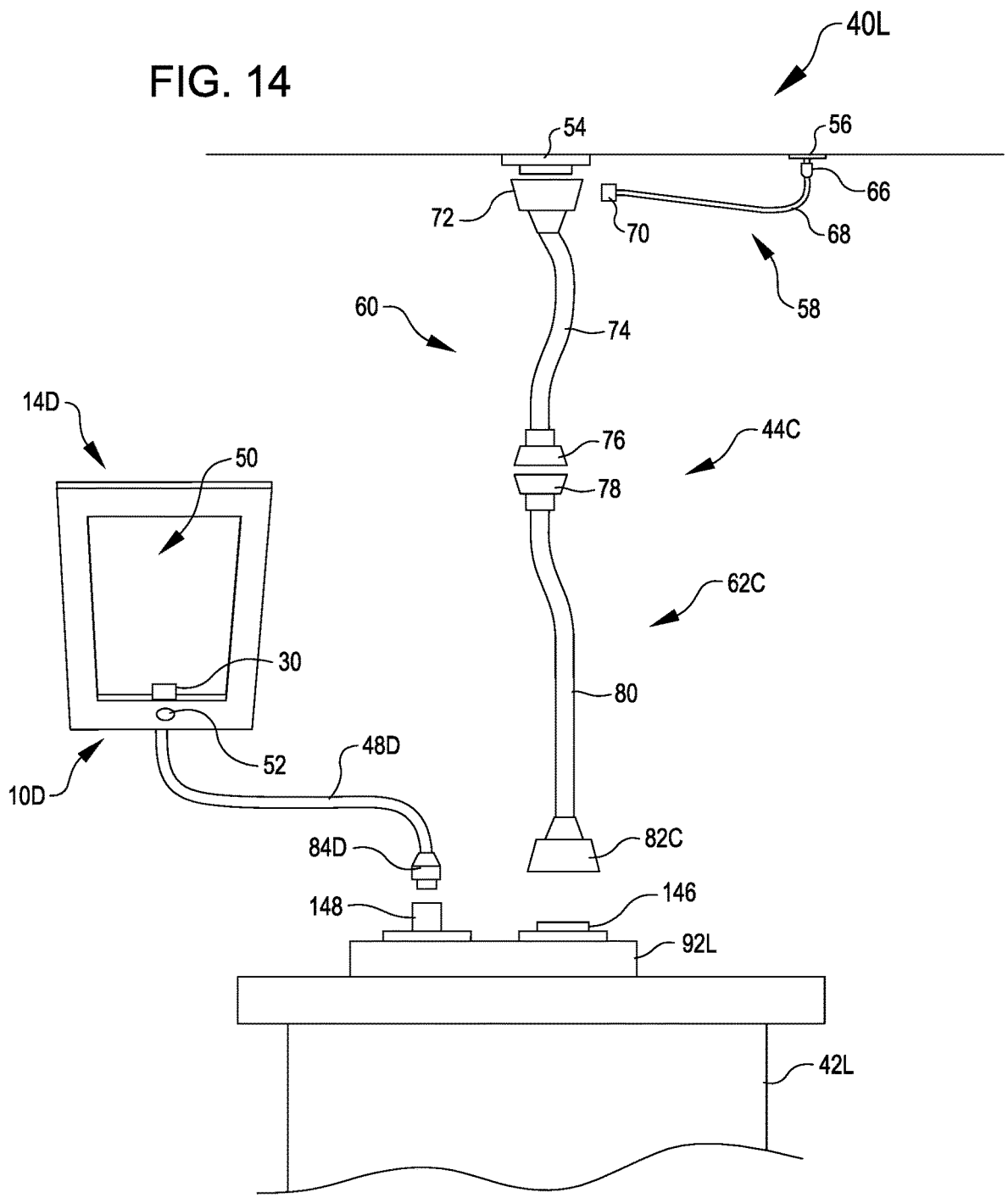
FIG. 14 shows a hospital room configuration in which a PED holder assembly is connected to a communication and power assembly for a patient bed, in accordance with embodiments, the PED holder assembly including a assistance request button.

FIG. 14 shows a hospital room configuration 40L that includes a hospital bed 42L, the communication and power assembly 44C, the PED holder assembly 10D. The bed 42L includes a bed hub 92L that includes a connector 146 and a connector 148. The distal connector 82C is connectable to the connector 146 to operatively connect the bed hub 92L to the assistance request communication system and the outlet 56. In some embodiments, the bed 42L includes any suitable number of assistance request buttons 52 that are operatively coupled with the assistance request communication system via the connector 146. The proximal connector 84D is connectable to the connector 148 to operatively connect the PED holder assembly 10D to the bed hub 92L and, thereby, to the assistance request communication system and the outlet 56 via the communication and power assembly 44C.

The hospital room configuration 40K can include any suitable number of quick disconnection features that enhance the ability to move the bed 42 and/or the PED holder assembly 10D. For example, in some embodiments, the distal connector 76 and the proximal connector 78 form a quick release connection, such as the magnetic connector disclosed in U.S. Pat. No. 9,147,965. In some embodiments, the distal connector 82C and the bed hub connector 146 form a quick release connection, such as the magnetic connector disclosed in U.S. Pat. No. 9,147,965. In some embodiments, the bed hub connector 148 and the proximal connector 84D form a quick release connection, such as the magnetic connector disclosed in U.S. Pat. No. 9,147,965.

Figure 15:
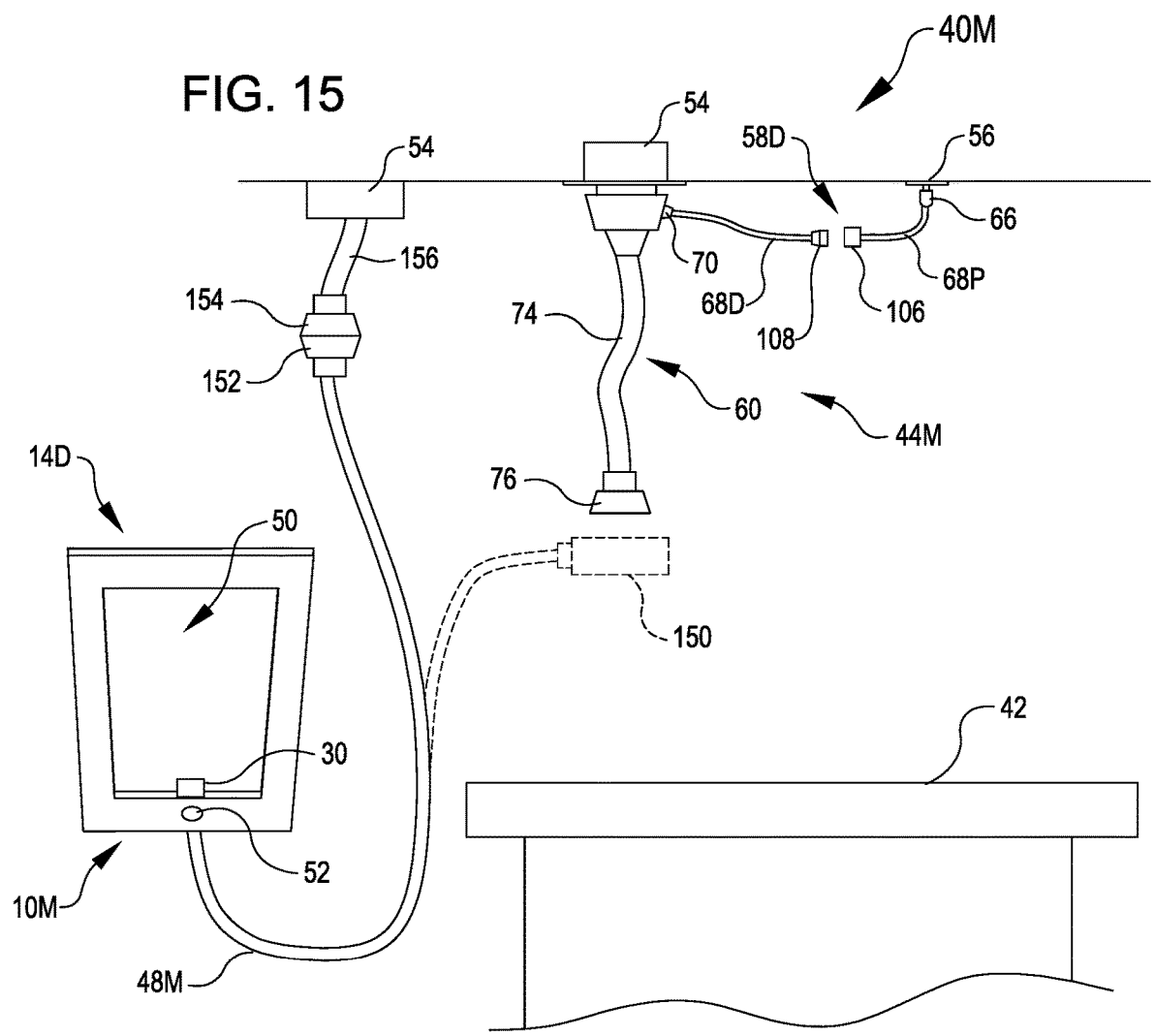
FIG. 15 shows a hospital room configuration that includes a PED holder assembly that can be connected to a communication and power assembly for a patient bed or connected directly to a power and/or data device that supplies power and/or data to a PED, in accordance with embodiments, the PED holder assembly including a assistance request button.

FIG. 15 shows a hospital room configuration 40M that includes a hospital bed 42, a communication and power assembly 44M, and a PED holder assembly 10M. The communication and power assembly 44M includes the PED power and/or data cable assembly 58D and the proximal cable assembly 60. The PED holder assembly 10M is configured similar to the PED holder assembly 10D. The PED holder assembly 10M includes the PED holder 14D, a power and communication cable 48M, and a proximal connector. In some embodiments, the proximal connector of the PED holder assembly 10M is a proximal coupler 150. The proximal coupler 150 is connectable to the distal connector 76 to operatively couple the PED holder 14D to the assistance request hub 54 and the power and/or data outlet 56 via the power and communication cable 48M. In some embodiments, the proximal connector of the PED holder assembly 10M is a proximal connector 152. The proximal connector 152 is connectable to a distal connector 154 to operatively couple the assistance request button 52 of the PED holder assembly 10M to a assistance request hub 54 via a connection cable 156. In some embodiments, the assistance request hub 54 supplies power to the PED holder 14D via a power transmission path including the connection cable 156, the distal connector 154, the proximal connector 152, the power and communication cable 48M, and the power and/or data output connector 30.

The hospital room configuration 40M can include any suitable number of quick connection features for operatively coupling the PED holder assembly 10M to a assistance request hub 54 or to both a assistance request hub 54 and a power and/or data outlet 56. For example, in some embodiments, the distal connector 76 and the proximal coupler 150 form a quick release connection, such as the magnetic connector disclosed in U.S. Pat. No. 9,147,965. In some embodiments, the distal connector 154 and the proximal connector 152 form a quick release connection, such as the magnetic connector disclosed in U.S. Pat. No. 9,147,965.

Figure 16:
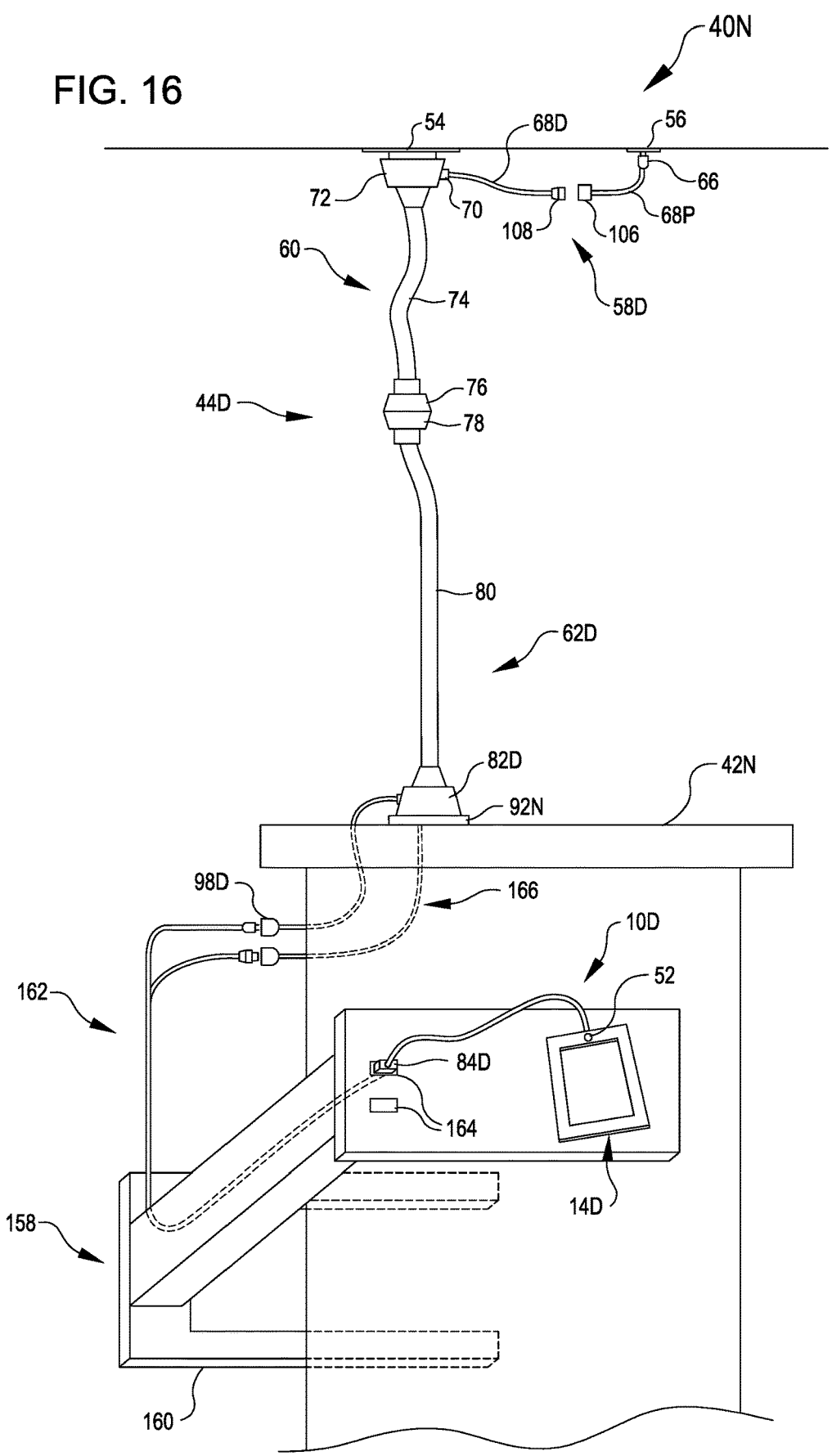
FIG. 16 shows a hospital room configuration in which a PED holder assembly is connected to a bed stand assembly connected to a communication and power assembly for a patient bed, in accordance with embodiments, the PED holder assembly including a assistance request button.

FIG. 16 shows a hospital room configuration 40M that includes a hospital bed 42N, the communication and power assembly 44D, the PED holder assembly 10D, and a bed stand assembly 158. The communication and power assembly 44D includes the PED power and/or data cable assembly 58D, the proximal cable assembly 60, and the distal cable assembly 62D. The bed 42N includes a bed hub 92N to which the distal connector 82D can be coupled to operatively couple the bed hub 92N to the assistance request hub 54 and the power and/or data outlet 56 via the communication and power assembly 44D.

The bed stand assembly 158 includes a bed stand 160, a connection cable assembly 162, and connection ports 164 mounted to the bed stand 160. The connection cable assembly 162 operatively couples each of the connection ports to both the bed hub 92N and the distal cable assembly 62D. In the illustrated embodiment, the connection cable assembly 162 is connectable to the bed hub 92N via a connection cable 166 to operatively couple each of the connection ports 164 to the assistance request hub 54 via the communication and power assembly 44D. Also in the illustrated embodiment, the connection cable assembly 162 is connectable to the distal connector 98D of the distal cable assembly 62D to operatively couple each of the connection ports 164 to the power and/or data outlet 56 via the communication and power assembly 44D. The proximal connector 84D of the PED holder assembly 10D is connectable to any one of the connection ports 164 to operatively couple the PED holder 14D to the assistance request hub 54 and the power and/or data outlet 56.

The hospital room configuration 40N can include any suitable number of quick disconnection features that enhance the ability to move the bed 42 and/or the bed stand assembly 158. For example, in some embodiments, the distal connector 76 and the proximal connector 78 form a quick release connection, such as the magnetic connector disclosed in U.S. Pat. No. 9,147,965.

Figure 17:
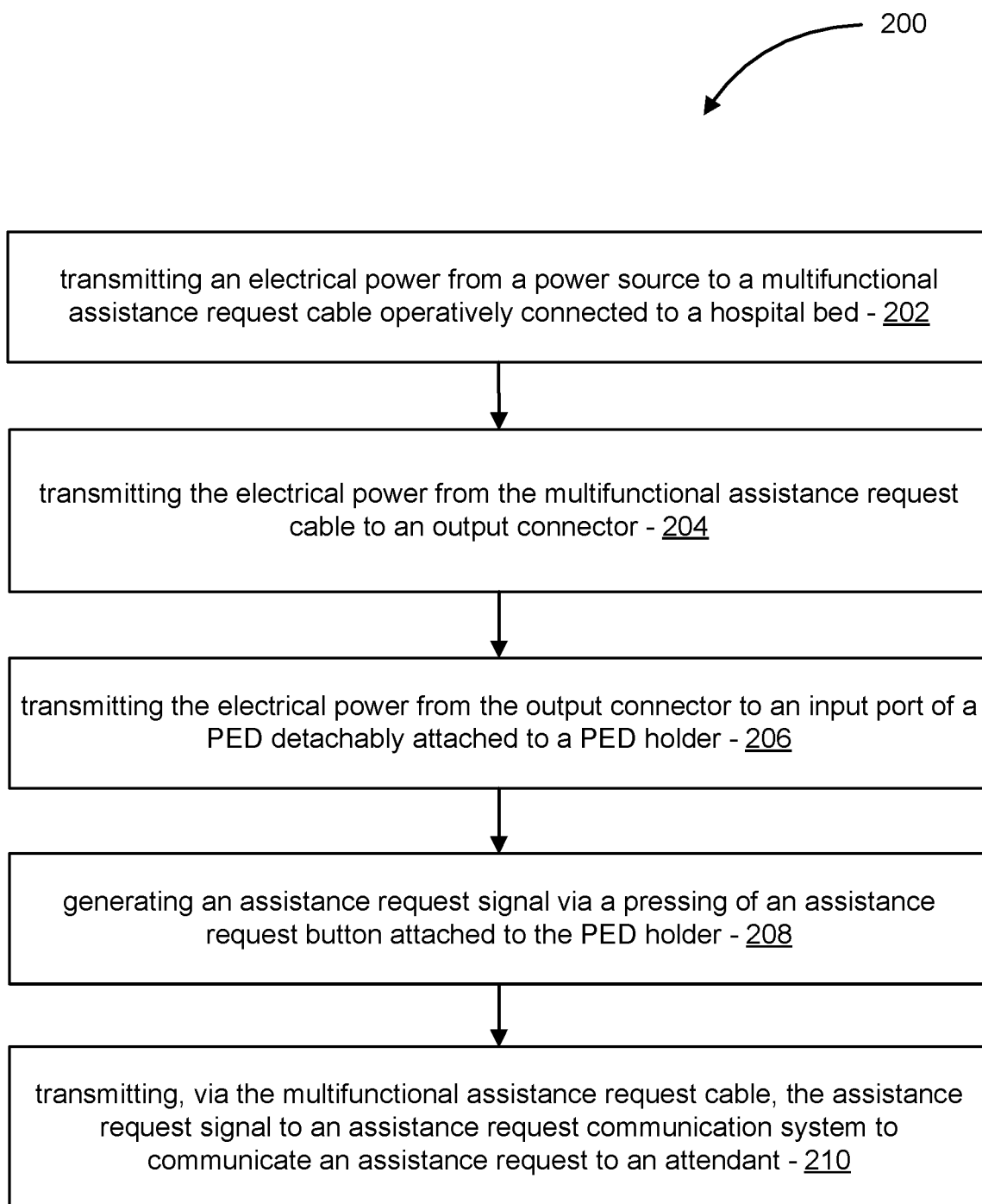
FIG. 17 is a simplified schematic diagram of a method of transmitting power to a portable electronic device (PED) over a multifunctional assistance request cable and a request for assistance signal over the multifunctional assistance request cable, in accordance with embodiments.

FIG. 17 is a simplified schematic diagram of a method 200 of transmitting power to a portable electronic device (PED) over a multifunctional assistance request cable and a request for assistance signal over the multifunctional assistance request cable, in accordance with embodiments. Any suitable assemblies, such as assemblies described herein, can be used to practice the method 200. The method 200 includes transmitting an electrical power from a power source to a multifunctional assistance request cable operatively connected to a hospital bed (act 202), transmitting the electrical power from the multifunctional assistance request cable to an output connector (act 204), transmitting the electrical power from the output connector to an input port of a PED detachably attached to a PED holder (act 206), generating an assistance request signal via a pressing of an assistance request button attached to the PED holder assembly (act 208), and transmitting, via the multifunctional assistance request cable, the assistance request signal to an assistance request communication system to communicate an assistance request to an attendant (act 210). Acts 202-210 can be accomplished using any suitable approach, such as the approaches described herein.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A portable electronic device (PED) holder assembly for use in a health care facility, comprising:
    a PED holder adapted to retain a PED;
    an assistance request button associated with requesting assistance in the health care facility, the assistance request button disposed in the PED holder;
    one or more interfaces adapted for connection to a power and data cable of the health care facility, the one or more interfaces disposed in the PED holder, wherein:
    a first interface of the one or more interfaces is operatively coupled with the PED such that power received from the power and data cable is provided from the first interface to the PED
    a second interface of one of the one or more interfaces is operatively coupled with a communication system of the health care facility such that an assistance request signal is provided from the second interface to the communication system via the power and data cable, and
    the second interface being the same as the first interface or different from the first interface.

2. The PED holder assembly of claim 1, wherein the one or more interfaces are further operatively coupled with the PED such that data received from the PED are provided from the one or more interfaces to the power and data cable.

3. The PED holder assembly of claim 1, wherein the second interface is different from the first interface, and wherein the PED is operatively coupled with the first interface while the assistance request button is operatively coupled with the second interface and while the first interface is operatively coupled with the second interface.

4. The PED holder assembly of claim 1, wherein the second interface comprises a connector assembly, wherein the power and data cable comprises a multifunctional assistance request cable, and wherein the connector assembly comprises a wall-side connector assembly adapted to be connected to a wall-side end of the multifunctional assistance request cable, the wall-side connector assembly being:
    adapted to operatively connect a power source to the multifunctional assistance request cable to transmit power received from the power source to the PED via the multifunctional assistance request cable; and
    adapted to connect the multifunctional assistance request cable to an assistance request communication system for transmission of the assistance request signal to the assistance request communication system to communicate a request for assistance.

5. The PED holder assembly of claim 4, wherein the wall-side connector assembly comprises a magnetic mechanism for detachably connecting the wall-side connector assembly to the wall-side end of the multifunctional assistance request cable.

6. The PED holder assembly of claim 4, wherein the wall-side connector assembly comprises a wall-side connector adapted to be connected to the wall-side end of the multifunctional assistance request cable, the wall-side connector comprising a wall-side PED connector and a wall-side assistance request signal communication connector, the wall-side PED connector being adapted to be operatively connected to a power source of the health care facility to transmit power through the multifunctional assistance request cable to the PED, the wall-side assistance request signal communication connector being adapted to be operatively connected to the assistance request communication system to transmit the assistance request signal from the multifunctional assistance request cable to the assistance request communication system.

7. The PED holder assembly of claim 4, further comprising the multifunctional assistance request cable.

8. The PED holder assembly of claim 7, wherein the multifunctional assistance request cable comprises a bed-side segment connected to the connector assembly, a wall-side segment connected to the wall-side connector assembly, and a magnetic mechanism for detachably connecting the bed-side segment to the wall-side segment.

9. The PED holder assembly of claim 1, wherein
    the assistance request button includes an illumination element that outputs light when power and/or data received from the power and data cable is transmitted to the PED.

10. The PED holder assembly of claim 1, further comprising a connection cable assembly and a bed connector adapted to attach to a side rail of a hospital bed, the bed connector being adapted to maintain a selected position of the connection cable assembly relative to the hospital bed.

11. The PED holder assembly of claim 1, further comprising a plurality of assistance request buttons, each one of the plurality of assistance buttons being operable to transmit an assistance request signal through the power and data cable to communicate a request for assistance.

12. The PED holder assembly of claim 1, wherein the power transmitted to the PED via the power and data cable is National Fire Protection Association (NFPA) 99 compliant.

13. The PED holder assembly of claim 1, wherein the assistance request button is operatively coupled with the first interface to transmit an input signal to the PED indicative of a pressing of the assistance request button.

14. A system for connecting a portable electronic device (PED) to a health care facility, comprising:
 a power and data cable operatively coupled to one or more systems of the health care facility;
 a PED holder to which the PED is detachably attachable, wherein:
  the PED holder comprises an assistance request button associated with requesting assistance in the health care facility, the assistance request button disposed in the PED holder;
  the PED holder comprises one or more interfaces,
  a first interface is operatively coupled with the PED such that power received from the power and data cable is provided from the first power interface to the PED,
  a second interface of one of the one or more interfaces is operatively coupled with a communication system of the health care facility such that an assistance request signal is provided from the second interface to the communication system via the power and data cable, and
  the second interface being the same as the first interface or different from the first interface.

15. The system of claim 14, wherein the PED holder further comprises a recess for retaining the PED, wherein the first interface is disposed in a side of the recess.

16. The system of claim 14, further comprising a plurality of assistance request buttons.

17. The system of claim 14, wherein the assistance request button is operatively coupled with at least one of the interface or the second interface.

18. The system of claim 16, wherein the first interface and the second interface operatively couple the power and data cable and the PED, and wherein the second interface operatively couples the power and data cable and the assistance request button.

19. The system of claim 14, further comprising an illumination element, wherein at least one of the first power and data interface and the second power and data interface operatively couples the illumination element and the power and data cable.

20. The system of claim 19, wherein an illumination state of the illumination element depends on transmission of at least one of the power or the data.

\* \* \* \* \*